United States Patent [19]

Paul et al.

[11] Patent Number: 5,658,753

[45] Date of Patent: *Aug. 19, 1997

[54] CATALYTIC ANTIBODY COMPONENTS

[76] Inventors: Sudhir Paul, 6824 S. 145th St., Omaha, Nebr. 68137; Michael J. Powell, 1024 Ocho Raos Dr., Danville, Calif. 94526; Richard J. Massey, 5 Valerian Ct., Rockville, Md. 20852; John H. Kenten, 1921 Windjammer Way, Gaithersburg, Md. 20879

[*] Notice: The term of this patent shall not extend beyond the expiration date of Pat. No. 5,229,272.

[21] Appl. No.: 402,158

[22] Filed: Mar. 9, 1995

Related U.S. Application Data

[63] Continuation of Ser. No. 57,491, May 4, 1993, abandoned, which is a continuation of Ser. No. 498,225, Mar. 23, 1990, Pat. No. 5,229,272, which is a continuation-in-part of Ser. No. 343,081, Apr. 25, 1989, Pat. No. 5,236,836.

[51] Int. Cl.$^6$ ............................... C12N 9/00; C12P 21/06
[52] U.S. Cl. .................. 435/68.1; 435/188.5; 435/219; 435/226; 530/388.24; 530/289.2
[58] Field of Search ........................... 435/188.5, 219, 435/226, 68.1; 530/389.2, 388.24

[56] References Cited

U.S. PATENT DOCUMENTS

| | | | |
|---|---|---|---|
| 4,196,265 | 4/1980 | Koprowski et al. | 435/2 |
| 4,376,110 | 3/1983 | David et al. | 436/319 |
| 4,492,751 | 1/1985 | Boguslaski et al. | 435/7 |
| 4,493,890 | 1/1985 | Morris | 435/7 |
| 4,659,567 | 4/1987 | Tramontano et al. | 424/85 |
| 4,661,586 | 4/1987 | Levy et al. | 530/387 |
| 4,792,446 | 12/1988 | Kim et al. | 424/85.8 |
| 4,888,281 | 12/1989 | Schochetman et al. | 435/72 |
| 4,900,674 | 2/1990 | Benkovic et al. | 435/232 |

FOREIGN PATENT DOCUMENTS

| | | |
|---|---|---|
| 125023 | 11/1984 | European Pat. Off. . |
| 0251093 | 1/1988 | European Pat. Off. . |
| 260939 | 3/1988 | European Pat. Off. . |
| WO86/06742 | 11/1986 | WIPO . |
| PCT/US89/01950 | 11/1989 | WIPO . |
| 8910754 | 11/1989 | WIPO . |
| WO90/05144 | 5/1990 | WIPO . |
| WO90/05746 | 5/1990 | WIPO . |

OTHER PUBLICATIONS

Altschuh, D. et al., "Localization of Antigenic Determinants of a Viral Protein by Inhibition of Enzyme-Linked Immunosorbent Assay (ELISA) with Tryptic Peptides", *J. Immunology Methods*, v. 50, p. 99 (1982).

Amit, A. G. et al., "Three-Dimensional Structure of an Antigen-Antibody Complex at 2.8 A Resolution", *Science* 233: 747 (1986).

Amzel, L. M. et al., "Three-Dimensional Structure of Immunoglobulins", *Ann. Rev. Biochem.* 48:961 (1979).

Anglister, J. et al., "NMR study of the Complexes Between a Synthetic Peptide Derived from the B Subunit of Cholera Toxin and Three Monoclonal Antibodies Against It", Abstract, *American Chemical Soc.* (1988), 006-2960/88/0427-0717.

Aruffo, A. et al., "Molecular Cloning of a CD38 cDNA by a high-efficiency COS cell expression system", *Proc. Natl. Acad. Sci.*, 84: 8573-8577 (1987).

Atassi, M. Z., "Surface-Simulation Synthesis and Its Application in Protein Molecular Recognition", *Protein Engineering-Applications in Science, Medicine and Industry*, pp. 125-153 Edited by Inouye, M. and Sarma, R., Academic Press (1986).

Azuma, T. et al., "Diversity of the Variable-Joining Region Boundary of λ Light Chains has a Pronounced Effect on Immunoglobulin Ligand-Binding Activity", *Proc. Natl. Acad. Sci. USA*, v. 81, p. 6139, (Oct. 1984).

Barrett, A. J., *Proteinase Inhibitors* (Editors A. J. Barrett and G. Salvesen), pp. 3-22, Elsevier, London, (1986).

Baum, R., "Catalytic Antibody Cuts Peptide Bond", *C & E N*, 5, 7-8 (1989).

Benjamini, E. et al., "Immunochemical Studies on the Tobacco Mosaic Virus Protein. VI. Characterization of Antibody Population Following Immunization with TMV Protein", *Biochemistry*, v. 7, No. 4, pp. 1253-1260 (1968).

Benjamini, E. et al., "Immunochemical Studies on the Tobacco Mosaic Virus Protein. VII. The Binding of Octanoylated Peptides of the TMV Protein with Antibodies to the Whole Protein", *Biochemistry*, v. 7, No. 4, pp. 1261-1264 (1968).

Better, M. et al., "*Escherichia Coli* Secretion of an Active Chimeric Antibody Fragment", *Science*, 240: 1041-1043 (1988).

Blackburn, G. M. et al., "Catalytic Antibodies", *Biochem. J.* 262: 381 (1989).

Bloom, S. R. et al., "Autoimmunity in Diabetics Induced by Hormonal Contaminants of Insulin", *Lancet* 1:14-17 (1979).Burd, J. et al., "Specific Protein-Binding Reactions Monitored by Enzymatic Hydrolysis of Ligand-Fluorescent Dye Conjugates", *Analytical Biochemistry*, 77, 56-67 (1977).

(List continued on next page.)

*Primary Examiner*—Charles L. Patterson, Jr.
*Attorney, Agent, or Firm*—John W. Ryan; Patrick J. Igoe; John L. Lemanowicz

[57] ABSTRACT

Catalytic antibody components, methods for producing catalytic antibody components, methods for using catalytic antibody components, in particular, single chain and smaller components are disclosed. Catalytic antibody components able to promote the cleavage or formation of an amide, peptide, ester or glycosidic bond, and which are prepared from monoclonal catalytic antibodies, catalytic autoantibodies or by site-directed mutagenesis are disclosed. Methods of using catalytic antibody components alone or in combination with other antibody components or other biological moieties are disclosed.

34 Claims, 15 Drawing Sheets

OTHER PUBLICATIONS

Chalufour, A. et al., "Rare Sequence Motifs are Common Constituents of Hypervariable Antibody Regions", *Ann. Inst. Pasteur/Immunology*, 138:671, Elsevier, Paris (1987).

Chaudhary, V. J. et al., "A recombinant immunotoxin consisting of two antibody variable domains fused to *Pseudomonas* exotoxin", *Nature* 339: 394 (1989).

Chothia, C. et al., "Canonical Structures for the Hypervariable Regions of Immunoglobulins", *J. Mol. Biol.* 196: 901 (1987).

Chothia, C. et al., "The Predicted Structure of Immunoglobulin D1.3 and Its Comparison with the Crystal Structure", *Reports*, 755 (Aug. 1986).

Cochran, A. G. et al., "Photosensitized Cleavage of a Thymine Dimer by an Antibody", *J. Am. Chem. Soc.*, 110: 7888–7890 (1988).

Colman, P. M. et al., "Three–Dimensional Structure of a Complex of Antibody with Influenza Virus Neuraminidase", *Nature* 326: 358 (Mar. 1987).

Corey, D. R. et al., "Generation of a Hybrid Sequence–Specific Single–Stranded Deoxyribonuclease", *Reports* 1401 (Dec. 1987).

David, G. S et al., "The Hybridoma–An Immunochemical Laser", *Clin. Chem.*, 27(9), 1580–1585 (1981).

de La Paz, P. et al., "Modelling of the Combining Sites of Three Anti–Lysozyme Monoclonal Antibodies and of the Complex Between One of the Antibodies and its Epitope", *EMBO J.*, 5:2, 415 (1986).

Dimaline, R. et al., "A novel VIP from elasmobranch intestine has full affinity for mammalian pancreatic VIP receptors", *Biochimica et Biophysica Acta*, 930, 97–100 (1987).

Dimaline, R. et al., "Purification and Characterization of VIP from Two Species of Dogfish", *Peptides*, 7 (Suppl. 1): 21–26 (1986).

Dixon, M. et al., *Enzymes*, Third Edition, London, (1979), index only.

Durfor, C. N. et al. "Antibody Catalysis in Reverse Micelles", *J. Am. Chem. Soc.* 110, 8713 (1988).

Edelman, G. M. et al., "Reconstitution of Immunologic Activity by Interaction of Polypeptide Chains of Antibodies", *Proc. Natl. Acad. Sci.*, 50: 753–761 (1963).

Emr, S. D. et al., "Sequence analysis of mutations that prevent export of $\lambda$ receptor, an *Escherichia coli* outer membrane protein", *Nature*, 285: 82–85 (1980).

Erhan, S. et al., "Do immunoglobulins have proteolytic activity?", *Nature*, v. 251, pp. 353–355 (Sep. 27, 1974).

Frackelton, Jr., A. R., et al., "Functional Diversity of Antibodies Elicited by Bacterial β–D Galactosidase", *J. Bio. Chem.*, 255 (11), 5286–5290 (1980).

Franek, F. and Nezlin, R. S., "Recovery of Antibody Combining Activity By Interaction of Different Peptide Chains Isolated from Purified Horse Antitoxins", *Folia Microbiol.*, 8: 128–130 (1963).

Gavish, M. et al., "Preparation of a Semisynthetic Antibody", Abstract, *Am. Chem. Soc.* (1978), 006–2960/78/0417–1345.

Geysen, H. M. et al., "A Priori Delineation of a Peptide Which Mimics a Discontinuous Antigenic Determinant", *Molecular Immunology*, 23:7 p. 709 (1986).

Giam, C. Z. et al., "In Vivo and In Vitro Autoprocessing of Human Immunodeficiency Virus Protease Expressed in *Escherichia Coli*", *J. Biol. Chem.*, 263: 14617–14620 (1985).

Gish et al., *J. Med. Chem.*, 14: 1159–1162, (1971).

Hansen, D., "Antibodies with Some Bite", *Nature*, 325, 304 (1987).

Harper, J. W. et al., "Enzymatically Active Angiogenin/Ribonuclease A Hybrids Formed by Peptide Interchange", Abstract, *Am. Chem. Soc.* (1988), 006–2960/88/0427–0219.

Hendershot, L. M. et al., "Identity of the Immunoglobulin Heavy–Chain–Binding Protein with the 78,000–Dalton Glucose–Regulated Protein and the Role of Posttranslational Modifications in Its Binding Function", *Mol. and Cellular Bio.*, 8(10), 4250–4256, (1988).

Highfeld, R., "AIDS Drug A Step Nearer", *The Daily Telegraph*, 9, (Aug. 4, 1987).

Hilvart, D. et al., "Catalysis of Concerted Reactions by Antibodies; The Claisen Rearrangement", *Proc. Natl. Acad. Sci. USA*, v. 85, pp. 4953–4955 (Jul. 1988).

Hochman, J. et al., "An Activity Antibody Fragment (Fv) Composed of the Variable Portions of Heavy and Light Chains", *Biochemistry* 12: 1130 (1973).

Huse, W. D. et al., "Generation of a Large Combinatorial Library of the Immunoglobulin Repertoire in Phage Lambda", *Science*, 246: 1275–1281 (1989).

Inbar, D. et al., "Localization of Antibody–Combining Sites within the Variable Portions of Heavy and Light Chains", *Proc. Natl. Acad. Sci. USA*, 69: 2659 (1972).

Inbar, D. et al., "Crystallization with Hapten of the Fab Fragment from a Mouse IgA Myeloma Protein with Antidinitrophenyl Activity", *J. of Biol. Chem.* 246: 6272 (1971).

Itoh, N. et al., "Human Preprovasoactive Intestinal Polypeptide Contains a Novel PHI–27–Like Peptide, PHM–27", *Nature* 304: 547–549 (1983).

Iverson, B. L. et al., "Sequence–Specific Peptide Cleavage Catalyzed by an Antibody", *Science* 243:1184 (1989).

Jackson, D. Y. et al., "An Antibody–Catalyzed Claisen Rearrangement", *J. Am. Chem. Soc.* 110, 4841 (1988).

Jacobs, J. et al., "Catalytic Antibodies", *J. Am. Chem. Soc.*, 109, 2174–2176 (1987).

Janda, K. D. et al., "Induction of an Antibody that Catalyzes the Hydrolysis of an Amide Bond", *Science* 241, 1188–1191 (1988).

Jaton, J. C. et al., "Recovery of Antibody Activity upon Reoxidation of Completely Reduced Polyalanyl Heavy Chains and Its Fd Fragment Derived from Anti–2,4–dinitrophenyl Antibody", *Biochemistry*, 7: 4185–4195 (1968)).

Jencks, W. P., "What Everyone Wanted to Know About Tight Binding and Enzyme Catalysis, but Never Thought of Asking", *Molecular Biol. Biochem. & Biophys.*, 32, 3–25 (1980).

Jencks, W. P., "Binding Energy, Specificity and Enzymic Catalysis: The Circe Effect", *Adv. Enzym.*, 43, 219–410 (1975).

Jencks, W. P., "Catalysis In Chemistry and Ezymology", 282–320, 288 (McGraw Hill, New York) (1969).

Jerne, N. K. et al., "Recurrent Idiotopes and Internal Images", *EMBO J.*, v. 1, No. 2, 243–247 (1982).

Kabat, E. A. et al., "Sequences of Proteins of Immunological Interest (5th Edition)", v. 1, 2, 3, U.S. Department of Health and Human Services (1991), Table of Contents only.

Knisley, K. A. et al., "Affinity Immunoblotting. High Resolution Isoelectric Focusing Analysis of Antibody Clonotype Distribution", *J. Immunological Methods*, 95, 79–87, Elsevier (1986).

Koerner and Nieman, "High Performance Liquid Chromatographic Determination of Glucosides", *J. Chromatography* 449, 216–228, (1988).

Kohen, F. et al., "Monoclonal Immunogloublin G Augments Hydrolysis of an Ester of the Homologous Hapten", *FEBS Letters*, 111, 427–431 (1980).

Kohen, F. et al., "Antibody–Enhanced Hydrolysis of Steroid Esters", *Biochimia et Biophysica Acta*, 629, 328–337 (1980).

Kohen, F. et a., "Nonradioisotopic Homogeneous Steroid Immunoassays", *J. Steroid Biochemistry*, 11, 161–167 (1979).

Kohen, F. et al., "A Steroid Immunoassay Based on Antibody–Enhanced Hydrolysis of a Steroid–Umbelliferone Conjugate", *FEBS Letters*, 100, 137–140 (1979).

Kohler, G. et al., "Continuous Cultures of Fused Cells Secreting Antibody of Predefined Specificity", *Nature*, 256: 445–497 (1975).

Kozbor, D. et al., "The Production of Monoclonal Antibodies from Human Lymphocytes", *Immunogy Today* 4:72–79, (1983).

Kozbor, D. et al., "Establishment of Anti-TNP Antibody–Producing Human Lymphoid Lines by Preselection for Hapten Binding Followed by EBV Transformation", *Scand. J. Immunol.*, 10:187–194, (1979).

Kubiak, T. et al., "Synthetic Peptides $V_H$ (27–68) and $V_H$ (16–68) of the Myeloma Immunoglobulin M603 Heavy Chain and their Association with the Natural Light Chain to Form an Antigen Binding Site", Abstract, *Am. Chem. Soc.* (1987), 006–2960/87/0426–7849.

Kwan, S. et al., "Production of Monoclonal Antibodies", *Genetic Engineering*, 2, 31–46, (1980).

Lee, F. et al., "Isolation and Characterization of a mouse interleukin cDNA clone that expresses B–cell stimulatory factor 1 activities and T–cell and mast–cell stimulating activities", *Proc. Natl. Acad. Sci. U.S.A.* 83: 2061–2065 (1986).

Lerner, R. A. et al., "At the Crossroads of Chemistry and Immunology: Catalytic Antibodies", *Science*, 252, 659–667 (May 1991).

Lerner, R. A. et al., "Catalytic Antibodies", *Scientific American*, 258(3), 42–50 (1988).

Lerner, R. et al., "Antibodies as Enzymes", *Trends Biochem. Science*, 12(11), 427–430 (1987).

Lerner, R. A., "Antibodies of Predetermined Specificity in Biology and Medicine", *Adv. In Immun.*, 36, 1–40 (1984).

Lorberboum–Galski, H. et al., "Cytotoxic Activity of an Interleukin 2–Pseudomonas Exotoxin Chimeric Protein Produced in *Escherichia coli*", *Proc. Natl. Acad. Sci. U.S.A.*, 85: 1922–1926 (1988).

Loh, E. Y. et al., "Polymerase Chain Reaction with Single–Sided Specificity: Analysis of T Cell Receptor δ Chain", *Science*, 243: 217–220 (1989).

MacDonald, R. J. et al., "Isolation of RNA Using Guanidinium Salts", *Meth. Enzymol.*, 152: 219–226 (1987).

Machleidt, W. et al., "Mechanism of Inhibition of Papain by Chicken Egg White Cystatin", (Biomedical Division, Elsevier Science Publishers), v. 243, No. 2, p. 234, (Jan. 1989) 00145793/89.

Mariuzza, R. A. et al., "The Structure Basis of Antigen–Antibody Recognition", *Ann. Rev. Biophys. Chem.*, 16: 139 (1987).

Marx, J., "Making Antibodies Work Like Enzymes", *Science* 234, 1497–1498 (1986).

Massey, R., "Catalytic Antibodies Catching On", *Nature*, 328 No. 6129, 457–458 (1987).

Meek, T. D. et al., "Inhibition of HIV–1 Protease in Infected T–Lymphocytes by Synthetic Analogues", *Nature*, 343: 96 (1990).

Melchers, F. et al., "Enhanced Stability Against Heat Denaturization of *E.Coli* Wild Type and Mutant β–Galactosidase in the Presence of Specific Antibodies", *Biochemical and Biophysical Research Communication*, 40(3), 570–575 (1970).

Mierendorf, R. C. et al., "Direct Sequencing of Denatured Plasmid DNA", *Meth. Enzymol.*, 152: 556–562 (1987).

Milstein, C., "Monoclonal Antibodies", *Scientific American*, 243(4), 66–74 (1980).

Moe, K., "Scripps, UC Create 'Killer' Antibodies", *S. D. Union*, (Dec. 12, 1986).

Mutter, M., "The Construction of New Proteins and Enzymes–A Prospect for the Future?", *Agnew. Chem. Int. Ed. Engl.* 24, p. 639 (1985).

Napper, A. "A Stereospecific Cyclization Catalyzed by an Antibody", *Science*, 237, 1041–1043 (1987).

Nilsson, A., "Structure of the Vasoactive Intestinal Peptide from Chicken Intestine. The Amino Acid Sequence", *FEBS Letters*, 60: 322–326 (1975).

Nishi, N. et al., "Apparent Autolysis of the N–Terminal Tetrapeptide of VIP", *Chem. Pharm. Bull.* 31(3), p. 1067 (1983).

Offord, R. E., "REVIEW Protein Engineering by Chemical Means?", *Protein Engineering*, v. 1, No. 5, p. 151 (1987).

Opstad, K., "The Plasma VIP Response to Exercise is Increased After Prolonged Strain, Sleep and Energy Deficiency and Extinguished by Glucose Infusion", *Peptides*, 8, 175–178 (1986).

Orlandi, R. et al., "Cloning Immunoglobulin variable domains for expression by the polymerase chain reaction", *Proc. Natl. Acad. Sci. U.S.A.*, 86: 3833–3837 (1989).

Paul, S. et al., "Affinity Chromatography of Catalytic Autoantibody to Vasoactive Intestinal Peptide", *J. Immunology*, v. 145, No. 4, pp. 1196–1199 (Aug. 1990).

Paul, S. et al., "Catalytic Hydrolysis of Vasoactive Intestinal Peptide by Human Autoantibody", *Science*, 244: 1158–1162 (1989).

Paul, S. et al., "Characterization of Autoantibodies to VIP in Asthma", *J. Neuroimmunology*, 23: 133–142 (1989).

Paul, S., "A New Effector Mechanism for Antibodies: Catalytic Cleavage of Peptide Bonds", *Cold Spring Harbor Symposium on Immunological Research*, v. 54 (1989).

Paul, S. et al., "Autoabzyme Catalyzed Cleavage of Vasoactive Intestinal Peptide", *Progress in Immunology*, v. VIII, pp. 833–836 (editors F. Melchers et al.), Springer Verlag, Verlin (1989).

Paul, S. et al., "Human Autoantibody to Vasoactive Intestinal Peptide: Increased incidence in Muscular Exercise", *Life Sciences* 43: 1079–1084 (1988).

Paul, S. et al., "Regulatory Aspects of the VIP Receptor in Lung", *Annals of New York Academy of Science*, v. 527, pp. 282–295 (Jun. 1988).

Paul, S. et al., "Elevated Levels of Atrial Natriuretic Peptide and Vasoactive Intestinal Peptide in Exercising Man", Abstract, *Clin. Res.*, 35: 112A (1987).

Paul, S. et al., "Characterization of Receptors for Vasoactive Intestinal Peptide from the Lung", *J. Biol. Chem.* 262: 158–162 (1987).

Paul, S. et al., "High Affinity Peptide Histidine Isoleucine–Preferring Receptors in Rat Liver", *Life Sciences*, v. 41, pp. 2373–2380 (1987).

Paul, S. et al., "Autoantibody to Vasoactive Intestinal Peptide in Human Circulation", *Biochem. Biophys. Res. Commun.* 130: 479–485 (1985).

Paul S. et al., "Purification of [$^{125}$I]–Vasoactive Intestinal Peptide by Reverse–Phase HPLC", *Peptides* 5: 1085–1087 (1987).

Pauling, L., "Nature of Forces Between Large Molecules of Biological Interest" *Nature*, 161: 707 (1948).

Pollack, S. J. et al., "Antibody Catalysis by Transition State Stabilization", *Cold Spring Harbor Symposium on Quantitative Biology*, 52, 97–104 (1987).

Pollack, S. J. et al., "Selective Chemical Catalysis by an Antibody", *Science*, 234, 1570–1573 (1986).

Porter, R. R. et al., "Subunits of Immunoglobulins and their relationship to Antibody Specificity", *J. Cell Physiol.*, 67 (Suppl. 1): 51–64 (1966).

Raso, V. et al., "The Antibody–Enzyme Analogy. Comparison of Enzymes and Antibodies Specific for Phosphopyridoxyltyrosine", *Biochemistry*, 14, 591–599 (1975).

Raso, V. et al., "The Antibody–Enzyme Analogy. Characterization of Antibodies to Phosphopyridoxyltyrosine Derivatives", *Biochemistry*, 14, 584–591 (1975).

Raso, V. et al., "Antibodies Specific for Conformationally Distinct Coenzyme Substrate Transition State Analogs.", *J. Am. Chem. Soc.*, 95(5), 1621–1628 (1973).

Rees, A. R. et al., "Investigating Antibody Specificity Using Computer Graphics And Protein Engineering", *Trends in Biochemical Sciences*, 11: 144 (Mar. 1986).

Rich, D. H., "Inhibitors of Aspartic Proteinases", *Proteinase Inhibitors* (Editors A. J. Barrett and G. Salvesen), Elsevier, pp. 179–217 (1986).

Roberts, S. et al., "The Cloning and Expression of an Anti–Peptide Antibody: A System for Rapid Analysis of the Binding Properties of Engineered Antibodies", (IRL Press Limited, Oxford, England) p. 59.

Roberts, R. J., "Directory of Restriction Endonuclease", *Methods in Enzymology*, 68, 27–31 (Academic Press, New York, R. Wu, Editor) (1979).

Roder, J. et al., "The EBV–Hybridoma Technique", *Methods in Enzymology*, 121: 140–167 (1986).

Roholt, O. et al., "Specific Combination of H and L Chains of Rabbit γ–Globulins", *Proc. Natl. Acad. Sci.*, 51: 173–178 (1964).

Rosselin, G., "The Receptors for the VIP Family Peptides (VIP, Secretin, GRF, PHI, PHM, GIP, Glucagon and Oxyntomodulin). Specificities and Identity.", *Peptides*, 7 (Suppl. 1): 89–100 (1986).

Royer G. P., "Enzyme–Like Synthetic Catalysts (Synzymes)", *Advances in Catalysis*, 29: 197–227 (1980).

Ruff, M. R. et al., "CD4 Receptor Binding Peptides that Block HIV Infectivity cause Human Monocyte Chemotaxis", *FEBS Letters*, 211: 17–22 (1987).

Sacerdote, P. et al., "Vasoactive Intestinal Peptide 1–12: A Ligand for the CD4 (T4) Human Immunodeficiency Virus Receptor", *J. of Neuroscience Res.*, 18: 102–107 (1987).

Sacks, D. L. et al., "Immunization of Mice Against African Trypanosomiasis Using Anti–Idiotypic Antibodies", *J. Expr. Med.*, 155, 1108–1119 (1982).

Sastry, L., et al., "Cloning of the immunological repertoire in *Escherichia coli* for generation of monoclonal catalytic antibodies", *Proc. Natl. Acad. Sci. U.S.A.*, 86: 5728–5732 (1989).

Schultz, P. G., "Catalytic Antibodies", *Acc. Chem. Res.*, 22: 287 (1989).

Schultz, P. G., "The Interplay Between Chemistry and Biology in the Design of Enzymatic Catalysts", *Science*, 240: 426 (1988).

Shenkin, P. S. et al., "Predicting Antibody Hypervariable Loop Conformation. I. Ensembles of Random Conformations for Ringlike Structures", *Biopolymers* 26: 2053 (1987).

Sheriff, S. et al., "Three–Dimensional Structure of an Antibody–Antigen Complex", *Proc. Natl. Acad. Sci. U.S.A.*, 84: 8075 (1987).

Shokar, K. M. et al., "A New Strategy for the Generation of Catalytic Antibodies", *Nature*, v. 338, pp. 269–271 (Mar. 1989).

Shokar, K. et al., "An Antibody–Mediated Redox Reaction", *Agnew. Chem. Int. Ed. Engl.* 27: 1172 (1988).

Skerra, A. et al., "Assembly of a Functional Immunoglobulin F$_v$ Fragment in *Escherichia coli*", *Science*, 240: 1038–1043 (1988).

Slobin, L., "Preparation and Some Properties of Antibodies with Specificity Towards p–Nitrophenylesters", *Biochemistry*, 5: 2836–2844 (1966).

Smith–Gill, S. J. et al., "Contributions of Immunoglobulin Heavy and Light Chains to Antibody Specificity for Lysozyme and Two Haptens", *J. Immunology*, 139: 4135 (1987).

Steinitz, M. et al., "Continuous Production of Monoclonal Rheumatoid Factor by EBV–Transformed Lymphocytes", *Nature*, 287: 443–445, (1980).

Steinitz, M. et al., "Establishment of a Human Lymphoblastoid Cell Line with Specific Antibody Production Against Group A Streptococcal Carbohydrate", *Immunobiology*, 156: 41–47 (1979).

Steinitz, M. et al., "EB Virus–Induced B Lymphocyte Cell Lines Producing Specific Antibody", *Nature* 269: 420–422 (1977).

Stewart, J. M. et al., "Solid Phase Peptide Synthesis", Pierce Chemical Co., Rockford, Illinois (1984), index only.

Summers, Jr. J. B., "Catalytic Principles of Enzyme Chemistry: Antibody Models and Stereo Electronic Control", Harvard University Ph.D. Thesis, 22–101 (1983).

Sun, L. K. et al., *Proc. Natl. Acad. Sci. U.S.A.*, 84: 214–218 (1987).

Tramontono, A. et al., "Antibody Catalysts Approaching the Activity of Enzymes", *J. Am. Chem. Soc.* 110: 2282 (1988).

Tramontono, A. et al., "Specificity and Mechanism of Esterolytic Antibodies", *J. of Cellular Biochemistry*, Supp. 11C, Abstract N 417, p. 238 (1987).

Tramontono, A. et al., "Antibodies as Enzymic Catalysts", *J. Cellular Biochemistry*, Supp. 11C, p. 199, Abstract N 022 (1987).

Tramontono, A. et al., "Catalytic Antibodies", *Science*, 234: 1566–1570 (1986).

Tramontono, A. et al., "Chemical Reactivity at an Antibody Binding Site Elicited by Mechanistic Design of a Synthetic Antigen", *Proc. Natl. Acad. Sci. U.S.A.*, 83: 6736–6740 (1986).

Turner, J. T. et al., D. B., "Characterization of the VIP Receptor in Rat Submandibular Bland: Radioligand Binding Assay in Membrane Preparations", *J. Pharmacol Exp. Therap.* 242, 873–881 (1987).

Unkeless, J. C. et al., "Structure and Function of Human and Murine Receptors for IgG", *Ann. Rev. Immunology*, 6: 251–281 (1988).

Van Brunt, J., "Antibodies Find a New Role . . . As Enzymes", *Biotechnology*, 5: 767 (1987).

Van der Eb, A. J. et al., "Assay of Transforming Activity of Tumor Virus DNA", *Meth. Enzymol.*, 65: 826–839 (1980).

Van Regenmortel, R. H. V., *Synthetic Peptides as Antigens*, Laboratory Techniques in Biochemistry and Molecular Biology Series (Editors R. H. Burdon and P. H. van Knippenberg), 19: 1–39 (1988).

Ward, E. S. et al., "Binding activities of a repertoire of single immunoglobulin variable domains secreted from *Escherichia coli*", *Nature*, 341: 544–546 (1989).

White, A. et al., *Principles of Biochemistry*, 200, 201, 217–221, 573, 575 and 585 (McGraw Hill Book Company, New York, Fourth Edition) (1968).

Winter, G. P., "Antibody Engineering", *Phil Trans. R. Soc. Lond.*, B 324, 537–547 (1989).

Woie, L. et al., "Increase in Plasma VIP in Muscular Exercise", *Gen. Pharmacol.*, 17: 321–326 (1987).

Wong, G. C. et al., "Human GM–CSF: Molecular Cloning of the Complementary DNA and Purification of the Natural and Recombinant Proteins", *Science*, 228: 810–815 (1985).

Yang, Y. C. et al., "Human IL–3 (Multi–CSF): Identification by Expression Cloning of a Novel Hematopoietic Growth Factor Related to Murine IL–3", *Cell*, 47: 3–10 (1986).

Yokota, T. et al., "Isolation and characterization of a human interleukin cDNA clone, homologous to mouse B–cell stimulatory factor 1, that expresses B–cell and T–cell stimulatory activities", *Proc. Natl. Acad. Sci. U.S.A.*, 83: 5894–5896 (1986).

"Abzylutely Spot On", *The Economist*, 80–81 (Feb. 7, 1987).

"Abzymes", *Scientific American*, 256, No. 2, 84–85 (1987).

*Affinity Chromatography Principles and Methods*, Pharmacia, pp. 12–18, Uppsala Sweden (1986).

"Antibody Catalyzes Stereospecific Reaction", Science/Technology Concentrates, *C&EN*, 15 (Aug. 31, 1987).

Bulletin Office Of Public Information, Berkeley Campus, University of California (Dec. 9, 1986).

"Cancer Breakthrough Seen —IGEN Discovers New Protein Class", *Rockville Gazette* (Jan. 21, 1987).

Baum, R., "Catalytic Antibodies Open Up New Strategy For Protein Engineering", Science, *C&EN*, 30–33 (Apr. 6, 1987).

*FPLC™ Ion Exchange and Chromatofocusing —Principles and Methods*, Phamacia, pp. 59–106, Uppsala, Sweden (1987).

"Making Antibodies Act Like Enzymes", *Science News*, 130, Nos. 25 & 26 (Dec. 20 & 27, 1986).

*PhastGel Silver Kit Instruction Manual*, Pharmacia, Uppsala, Sweden (1987).

Berchtold et al., *Blood* vol. 74, No. 7, pp. 2414–2417 (1989).

Edwards et al., "Human Monoclonal Antibodies and the Selection AF Antigens Suitable for Therapy" in *Monclonal Antibodies '84: Biological and Clinical Applications: Proceedings of the International Symposium on Monoclonal Antibodies '84* held in Florence, Italy, Oct. 16–19, 1984.

Klein, J., Immunology, John Wiley & Sons, N.Y. 1982, pp. 168–169.

Baldwin, E., et al. (1989) Science 245, 1104–1107.

Jackson, D.Y. et al. (1991) Proc. Natl. Acad. Sci. USA 88(1), 58–62.

Shuster, A.M., et al. (1992) Science 256, 665–667.

CATALYTIC ANTIBODY COMPONENTS

This application is a continuation of U.S. patent application Ser. No. 08/057,491, filed May 4, 1993, abandoned, which is a continuation of U.S. patent application Ser. No. 07/498,225 filed Mar. 23, 1990, U.S. Pat. No. 5,229,272, which is a continuation-in-part of U.S. patent application Ser. No. 07/343,081 filed Apr. 25, 1989 now U.S. Pat. No. 5,236,836.

FIELD OF THE INVENTION

This invention pertains generally to components of antibodies capable of catalytically enhancing the rate of a chemical reaction. More specifically, this invention relates to components of catalytic antibodies, e.g., heavy and light chains, which are capable of catalytically enhancing the rate of a chemical reaction. This invention also relates to methods for obtaining the catalytic components.

Several publications are referenced in this application by Arabic numerals within parentheses in order to more fully describe the state of the art to which this invention pertains as well as to more fully describe the invention itself. Full citations for these references are found at the end of the specification immediately preceding the claims.

BACKGROUND OF THE INVENTION

Antibodies are well known to bind antigens and it is generally recognized that the antigen-binding segment of antibodies is composed of the variable portion of a heavy (H) and a light (L) chain. Both of these chains are thought to be important in defining the paratope conformation to one that binds antigen with high affinity. It has recently been found that antibodies can catalytically enhance the rate of chemical reactions. In U.S. Pat. No. 4,488,281, it is disclosed that catalytic antibodies can bind a substrate, cause the conversion thereof to one or more products, and release the product. The catalytic antibodies may be prepared by immunological methods wherein they are elicited to antigens, as taught, for example, in U.S. Pat. No. 4,888,281.

Fab fragments of an antibody catalyze hydrolysis of an amide bond (1). Fv fragments, which are heterodimers consisting of the variable regions of associated light and heavy chains of an antibody, have been shown to catalyze ester hydrolysis (2). These antibody components are not known to catalyze the cleavage or formation of peptide bonds, a class of reactions which is energetically more demanding.

Iverson and Lerner (3) report that while peptide bond cleavage is very energetically demanding, cleavage of a peptide bond by a catalytic antibody is enabled by the presence of a metal trien cofactor and will not take place without the presence of such a cofactor. The trien complexes of Zn(II), Ga(III), Fe(III), In(III), Cu(II), Ni(II), Lu(III), Mg(II) or Mn(II) were most favored. However, a naturally occurring autoantibody able to selectively catalyze the cleavage of the peptide bond between amino acid residues 16 and 17 of the neurotransmitter vasoactive intestinal peptide (VIP) without any metal cofactor, has been reported by Paul (4, 5).

It is also known that antibody binding is energetically most favored by the presence of the entire H-chain and L-chain binding site (6). The $V_H$ fragments of anti-lysozyme antibodies bind the antigen with an affinity of only 10% of the intact antibody (7). L-chains are also likely to participate in antigen binding interactions, although most studies suggest that the contribution of L-chains is smaller than that of H-chains (8–10). It could not be expected that an antibody component smaller than an intact catalytic antibody would possess the favorable steric conformation provided by the intact catalytic antibody to permit the catalysis of a peptide bond without the assistance of a metal trien cofactor as taught by Lerner and Iverson.

The reports of Fv and Fab catalysis of ester and amide bonds do not disclose that other types of heterodimers catalyze any chemical reactions (8–10). A heterodimer not known or expected to catalyze chemical reactions is the heterodimer consisting of an intact H-chain and intact L-chain linked by at least one disulfide (S—S) bond. Another heterodimer not known or expected to catalyze chemical reactions is a heterodimer analogous to the Fab, but consisting of the Fd- fragment (the H-chain with the Fc portion removed) linked to or associated with an intact L-chain by non-covalent bonding (e.g. hydrogen bonding, charge interaction or similar association), in contrast to the Fab which consists of the Fd fragment linked to the L-chain by at least one disulfide bond.

Heavy chain homodimers and light chain homodimers have heretofore not been shown to catalyze chemical reactions. It would not be expected that these homodimers would have catalytic activity because the classic binding function of antibodies is considered to require the combination of the variable regions of both a light and heavy chain, or at least a heavy chain (8, 11–13). Catalytic light and heavy chain homodimers would be advantageous because they consist of the same or similar components, and thus could be manufactured with less effort than is required to manufacture a standard antibody or a heterodimer.

There are obvious advantages that single chain proteins offer over multichain proteins (antibodies), both from the point of view of structure-function analysis as well as pharmacological and therapeutic stability. It would be advantageous if the binding and catalytic domains on an antibody were either the same or closely positioned to one another such that the benefits of catalytic activity could be achieved by a simple protein as opposed to a multichain antibody. Heretofore, the art has not demonstrated the capability of using such components of an antibody for catalytic purposes. Similar advantages are offered by dimers formed of the several combinations of light and heavy chains.

It is known to use a catalytic antibody to convert a prodrug to a drug (14). However, a catalytic component able to convert a prodrug to a drug, or a protoxin to a toxin has special advantages, particularly when the catalytic component is incorporated into a fusion or chimeric protein with a biological binding agent able to bind to cells or tissues which it is desirable to contact with the drug or toxin.

OBJECTS OF THE INVENTION

It is therefore a general object of the invention to provide components of antibodies which enhance the rate of a chemical reaction.

It is a further object of the invention to identify components of catalytic antibodies which enhance the rate of a chemical reaction and which are simpler in structure than the catalytic antibodies from which they are obtained or which heretofore have been used for catalysts.

It is still a further object of the invention to provide methods for obtaining components of catalytic antibodies, which components retain the catalytic activity of the parent antibody and which can be used to enhance the rate of chemical reaction.

It is still a further object of the invention to provide a variety of methods for obtaining catalytic components of catalytic antibodies.

3

It is still a further object of the invention to conduct chemical reactions using catalytic components of catalytic antibodies.

SUMMARY OF THE INVENTION

The invention is broadly directed to components of antibodies which enhance the rate of a chemical reaction. The components of the antibody which have been found to be catalytic include the Fab portion of an antibody, the Fv portion thereof, a light chain, a heavy chain, a mixture of the unassociated light and heavy chains, dimers formed of the various combinations of light and heavy chains, a variable fragment of a light chain, a variable fragment of a heavy chain, a catalytic domain of a light chain, and a catalytic domain of a heavy chain. These components can catalyze reactions with high turnover and without themselves entering into the reactions and are advantageous over whole catalytic antibodies.

The catalytic components can be obtained in a number of different ways. Broadly, the components can be obtained from whole catalytic antibodies or autoantibodies which are created in methods known in the art, including immunological methods employing transition state analog compounds to elicit the antibodies. The catalytic components, e.g., light or heavy chains of a catalytic antibody, can be prepared by cleaving purified antibody into certain fractions and then reducing and alkylating those fractions to cleave the bonds connecting the light and heavy chains. In still other methods, the sequence of the variable region of a catalytic antibody is determined and a gene coding for the variable region of the catalytic antibody is inserted into a cell and the variable region is then expressed in said cell.

DETAILED DESCRIPTION OF THE INVENTION

Definitions

Figure 1:
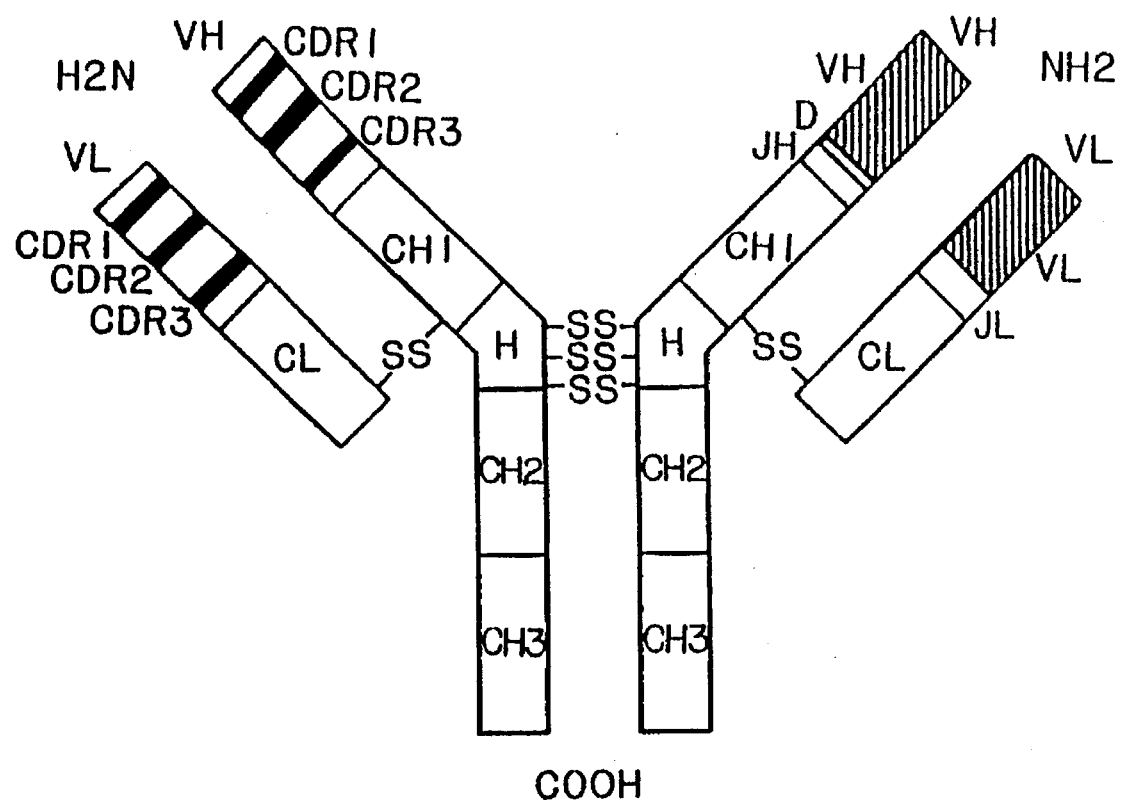
FIG. 1. Diagram of a prototypical IgG molecule.

Chemical reaction refers to a reaction wherein at least one reactant is converted to at least one product. Such chemical reactions include chemical reactions which can be catalyzed by enzymes such as, for example, oxoreductases, transferases, hydrolases, lyases, isomerases and ligases as well as chemical reactions for which no catalytic enzymes are known, such as, for example, oxidations, reductions, additions, condensations, eliminations, substitutions, cleavages and rearrangements.

The term "animal" as used herein refers to any organism with an immune system and includes mammalian and non-mammalian animals. The term "substrate" is synonymous with the reactant in the chemical reaction and can be any of a number of molecules and biomolecules including but not limited to proteins, phospholipids, carbohydrates (e.g., glycogen, glucose, etc.), drugs (including abused substances and drugs from exogenous sources).

Antibody and immunoglobulin refer to any of several classes of structurally related proteins that function as part of the immune response of an animal, which proteins include IgG, IgD, IgE, IgA, and IgM and related proteins. Antibodies are found in plasma and other body fluids and in the membrane of certain cells. Under normal physiological conditions (e.g. absent immunological dysfunction or human intervention) antibodies are produced by B cells (or the functional equivalent) of an animal in reaction to the entry of proteins or other chemical substances which that animal is not immunologically tolerant of into the tissue or body fluids of that animal.

The examples of preferred embodiments of the present invention generally relate to IgG. However, the terms antibody and immunoglobulin as used herein refer to any class of antibody, including IgD, IgE, IgA, IgM and related classes and subclasses. An antibody as described above may also be referred to as a "physiological antibody" in order to clearly distinguish an intact antibody, as is normally produced by an animal, from the antibody components of the present invention.

Autoantibodies in accordance with the invention may be naturally occurring antibodies produced by the immune system of an animal which bind to the animal's own cellular components and which are not elicited by specific immunization against a target antigen. Autoantibodies recognize a self-antigen, i.e., any antigen which the body makes using its own genetic code. Thus, self-antigens are distinguished from foreign antigens (e.g., bacterial, viral antigens). The term "substrate" as defined herein can be the same as or different from the self-antigen.

Peptide bond as used herein refers to an amide bond linking two adjacent amino acid residues and is generically represented by the following formula:

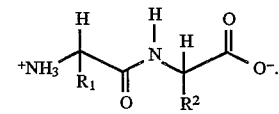

An amino acid consists of a carbon atom to which is bonded an amino group, a carboxyl group, a hydrogen atom and a distinctive group referred to as a "side chain" ($R_1$ and $R_2$ in the formula above). Amino acid as used herein includes the twenty naturally occurring amino acids which comprise the building blocks of proteins. It is understood by those skilled in the art that when either of the adjacent amino acids is proline, the respective side chains $R_1$ or $R_2$ are bonded to the adjacent nitrogen atoms to form the characteristic 5-membered proline ring.

The substrate containing the peptide bond or bonds to be cleaved can be any proteinaceous molecule such as, for example, a regulatory protein or a structural protein, and includes, but is not limited to, peptide hormones (e.g., insulin, growth hormone, secretin, etc.), peptide neurotransmitters and neuromodulators (e.g., vasoactive intestinal peptide, endorphins, enkephlins, bradykinins, substance P etc.) tumor proteins (e.g., oncogene products, carcinoembryonic antigens, etc.), bacterial proteins and viral proteins (e.g., human immunodeficiency viral(HIV) gp 120, influenza glycoproteins, etc.).

The rate enhancement achieved by the antibody components according to the invention is either catalytic or stoichiometric. Thus, components which catalytically enhance the rate of the reaction are "catalytic components" and components which stoichiometrically enhance the rate of the chemical reaction are "stoichiometric components".

A catalytic component part of an antibody in accordance with the invention is a substance which is capable of changing the rate of a chemical reaction, all other conditions (e.g., temperature, reactant/substrate concentration, etc.) being the same and which does not enter into the chemical reaction and therefore is not consumed in the reaction. It is also a substance which exhibits the capability of converting multiple moles of reactant/substrate per mole of catalytic component part; which, from a mechanistic viewpoint, binds the reactant/substrate, effects the accelerated conversion of the reactant/substrate to the product and then releases the product; and which changes the rate of the chemical reaction without shifting the position of the equilibrium. The aforementioned definitions are characteristics of ideal catalysts. However, in practice, even the best of catalysts become poisoned or deactivated by contamination in the reaction system or as a result of chemical or physical destruction during the reaction process. For reasons well known in the art, the true operation of a catalyst may be obscured by components of the reaction system or by the condition of the reaction environment.

A stoichiometric component part in accordance with the invention enhances the rate of the chemical reaction stoichiometrically. It enhances the rate of the reaction but, unlike a catalytic component, is stoichiometrically consumed during the reaction. Thus, the term "stoichiometric enhancement" implies that the component causing the observed rate enhancement enters into the reaction as a reactant and is consumed in the process.

The art has adopted certain working definitions to express catalytic activity. These expressions are [1] $k_{cat}$, or "turnover" and [2] $k_{cat}/k_{uncat}$, the "rate enhancement factor". Turnover indicates the number of molecules of reactant/substrate which can be converted to product per mole of catalytic component per unit time. For example, if a molecule exhibits a turnover of $10^3$ molecules of substrate per minute and the molecule maintains its catalytic activity for 24 hours at room temperature and at its optimal pH, each molecule of catalyst would then make a total of $1.4 \times 10^6$ conversions, indicating its catalytic behavior. This total conversion is to be distinguished from the total conversion in a stoichiometric reaction, which will never exceed 1.0, no matter how long the reaction is carried out. The rate enhancement factor is a dimensionless number which expresses the rate of reaction in the presence of catalyst to the rate of reaction in the absence of catalyst, all other reaction conditions (e.g., reactant concentration, temperature, etc.) being equal.

Reference has been made to component parts of an antibody. These component parts are also correctly referred to as fragments or antibody fragments. These parts are defined by way of example with reference to the IgG molecule, but it will be understood by those skilled in the art that these components may be derived from any of the other antibody classes (IgA, IgE, IgD, IgM and related classes and subclasses). The IgG molecule may be described as a "Y" shaped protein made up of four polypeptide chains linked together by disulfide bonds (FIG. 1). The tops of the "Y" are the N-terminals of the protein chains which comprise IgG tetramer. Two identical heavy chains (also known to the art as gamma chains, hereinafter H-chains) extend from the stem of the "Y" into the arms; two identical light chains (also known to the art as kappa or lamda chains depending on their antigenic structure, hereinafter L-chains) are confined to the arms. Each polypeptide has both constant regions (C regions) and variable regions (V regions). The V regions are located in the N-terminal domains of the H and L-chains. In the V region are three areas of greatest sequence variability known as the hypervariable or complementarity determining regions ("CDRs"). The H- and L-chain CDRs together form the antigen binding site. Sequence variability in chain CDRs underlies the range of antibody specificities that the immune system produces. All antibodies of a given type have the same constant regions, but the variable regions differ from one clone of B cells to another. At the end of each arm, the L- and H-chain variable regions fold to create an antigen binding site comprising the CDRs as described above. The H-chains are about 50 kD in size, and the L-chains are about 25 kD in size.

The point at which the H-chains separate to form the top of the "Y" is known to the art as the hinge region. The IgG may cleaved by papain enzyme above the hinge region (11) into two Fab fragments and one Fc fragment. As described above, the top of the "Y" is known to include the variable region, which performs the specific binding function of the antibody. The Fc fragment represents the bottom of the "Y" and serves complement fixation and other non-binding functions. The Fab fragment is a heterodimer cleaved from each side of the top of the "Y", and is formed of intact L-chains and of an approximately 25 kD partial H-chain known to the art as an Fd fragment.

The Fv fragment is a 25 kD heterodimer similar in structure to the Fab fragment described above, but consisting of shorter segments of the N-terminal sequences of the H- and L-chains respectively from the top of the "Y" (15). The Fv includes the variable regions of the constituent H- and L-chain fragments.

The Fv fragment, in turn, may be separated into two approximately 12.5 kD single chain fragments or components referred to as a variable fragment of an H-chain ($V_H$) and a variable fragment of an L-chain ($V_L$) (15).

The H- and L-chain components may be separated from an intact antibody as complete unassociated chains, or may be produced de novo as complete unassociated chains by one of the recombinant genetic techniques known to the art from a gene coding for an L- or H-chain, or may be produced by B cells or hybridoma cells selected for the property of producing unassociated H- or L-chains. These unassociated H and L chains may then be used according to the present invention as non-associated catalytic chains, or may be allowed to associate by methods known to the art to produce H/L heterodimers, H/H homodimers, or L/L homodimers.

The variable fragment of the H- or L-chain is the peptide sequence containing the variable region, and may be further reduced to a minimum peptide sequence defining the variable domain which retains the binding property inherent in that amino acid sequence.

The catalytic domain is the minimum peptide sequence which retains the catalytic property inherent in that amino acid sequence.

Each of these components may be sequenced and expressed by recombinant methods known to the art. The catalytic domain may be usefully recombined by recombinant technology with other useful genetic sequences to produce chimeric proteins with catalytic properties. The catalytic components may be produced de novo by means of mutagenesis techniques known to the art applied to the genetic sequences of antibody H- or L-chain variable domains either before or after the genetic sequence for a variable domain has been inserted in a host cell.

The catalytic component parts may be associated with molecules having functions different from the component parts, or may be associated with each other. "Associated" or "associate" when used to describe the relationship between component parts or other molecules means either covalent binding (for example, disulfide bonds or other chemical bonds well known to the art) or non-covalent binding (for example, hydrogen bonding, charge interaction or other non-covalent binding well known to the art). The terms associated or associate may be qualified. For example, "associated non-covalently" refers only to components or other molecules which are non-covalently bound. The term "unassociated" refers to components or molecules which are not linked by either covalent or non-covalent bonding.

DETAILED DESCRIPTION OF THE DRAWINGS

FIG. 1. Diagram of a prototypical IgG molecule. Note that the COOH terminal comprises the Fc portion of the antibody. The junction of the "Y" is the hinge region. The H2N termini represent the variable regions which are critical to antigen-specific binding.

Figure 2:
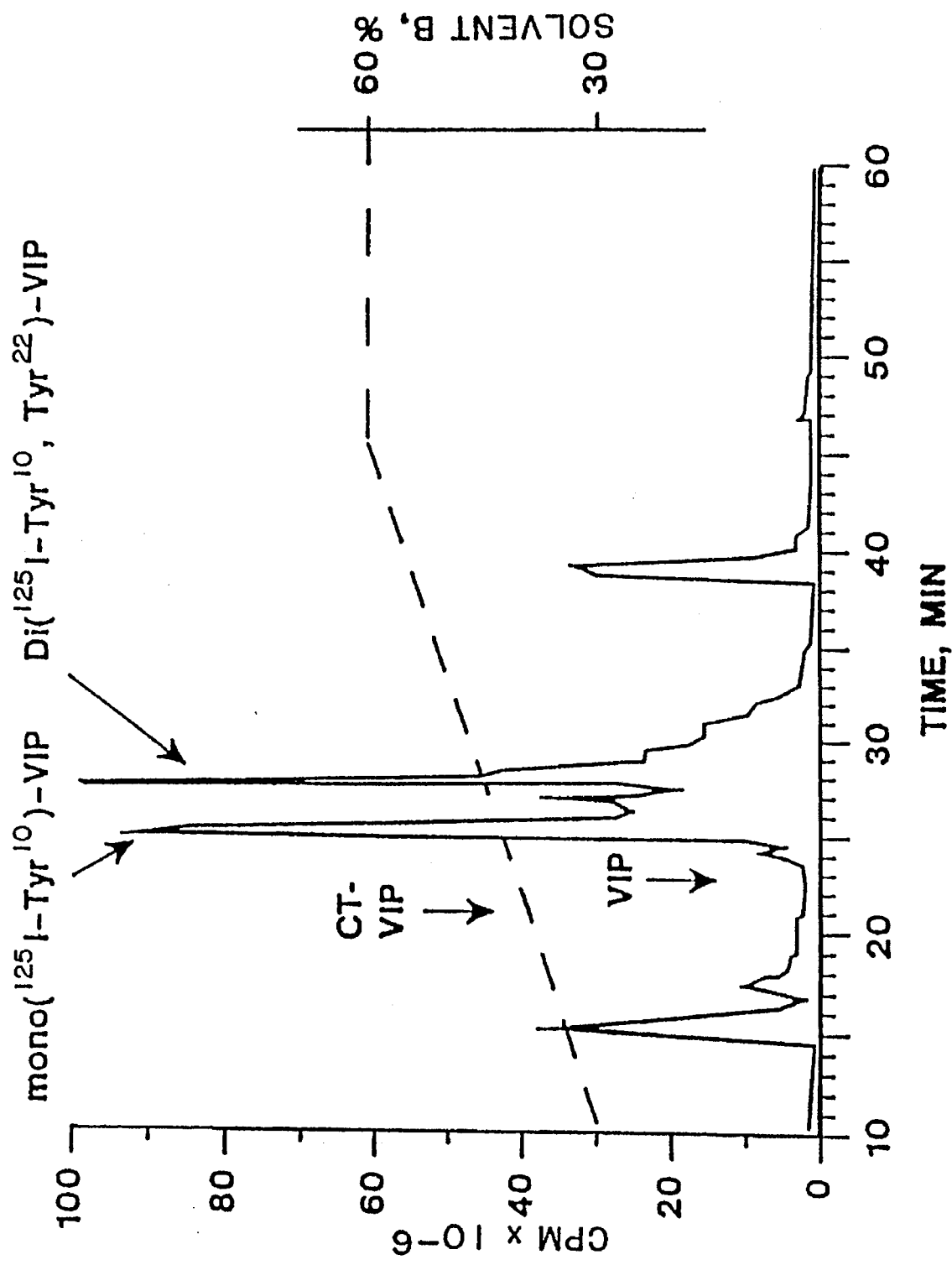
FIG. 2. Reverse phase HPLC Purification of mono ($^{125}$I-TYR$^{10}$)-VIP.

FIG. 2. Reverse phase HPLC Purification of mono ($^{125}$I-TYR$^{10}$)-VIP.

Figure 3A:
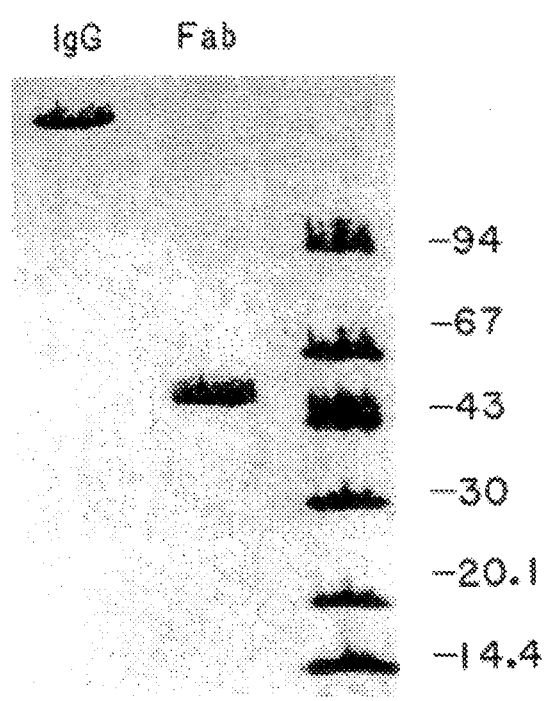
FIGS. 3A–3B. VIP hydrolytic activity resides in the Fab Fragment.
Figure 3B:
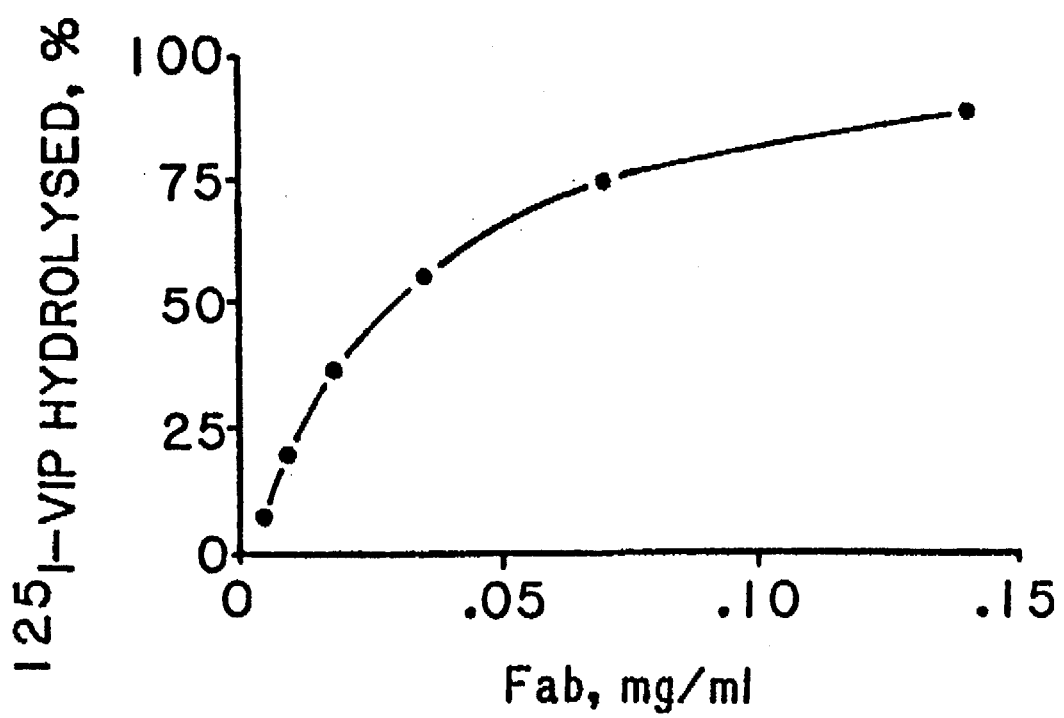

FIGS. 3A and 3B. VIP hydrolytic activity resides in the Fab Fragment.

FIG. 3A. Silver stained SDS-PAGE of IgG, Fab VIP.

FIG. 3B. Hydrolytic activity resides in the Fab fragment.

Figure 4A:
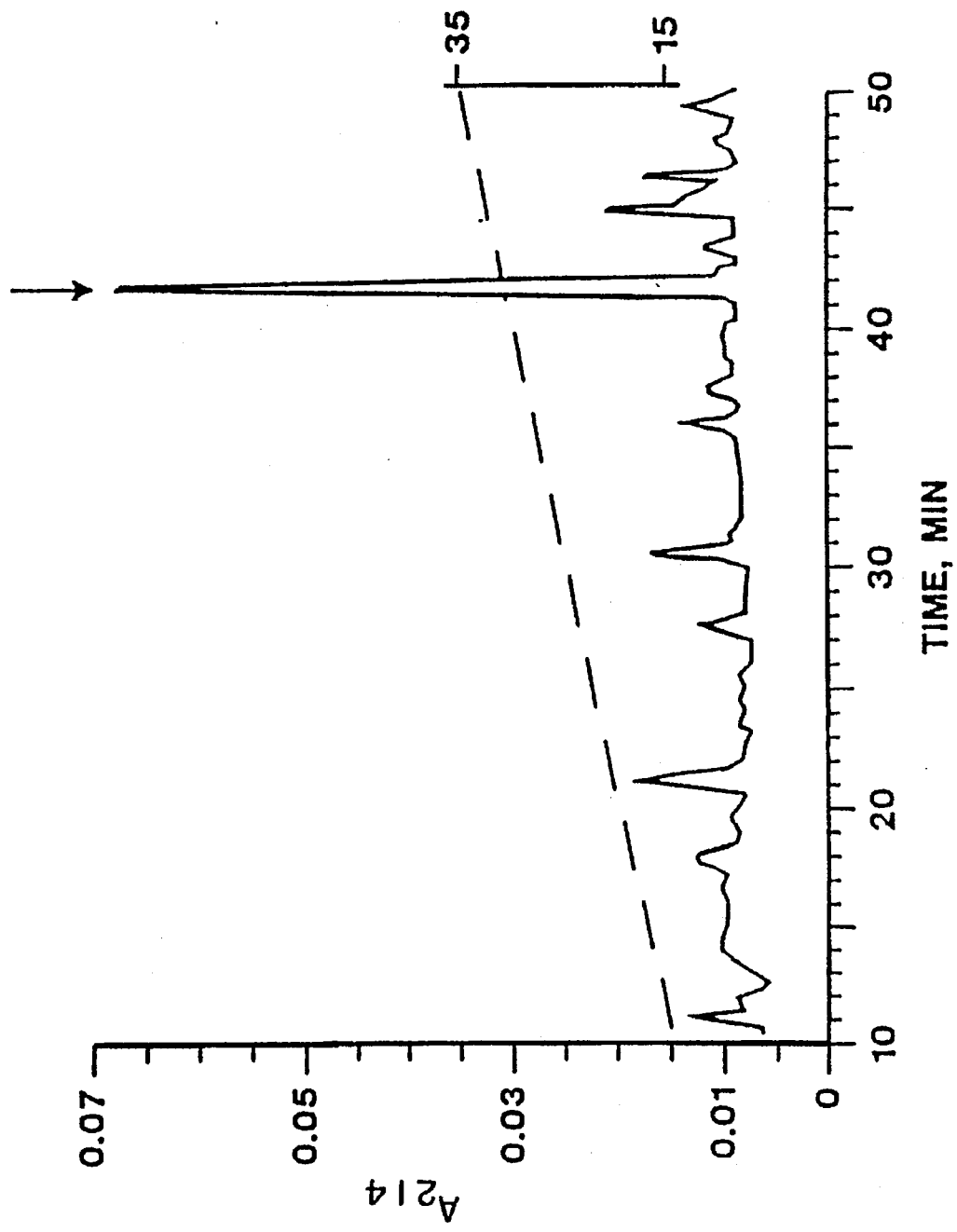
FIGS. 4A–4B. Identification of VIP fragments produced by IgG and comparing catalytic IgG and non-catalytic IgG.
Figure 4B:
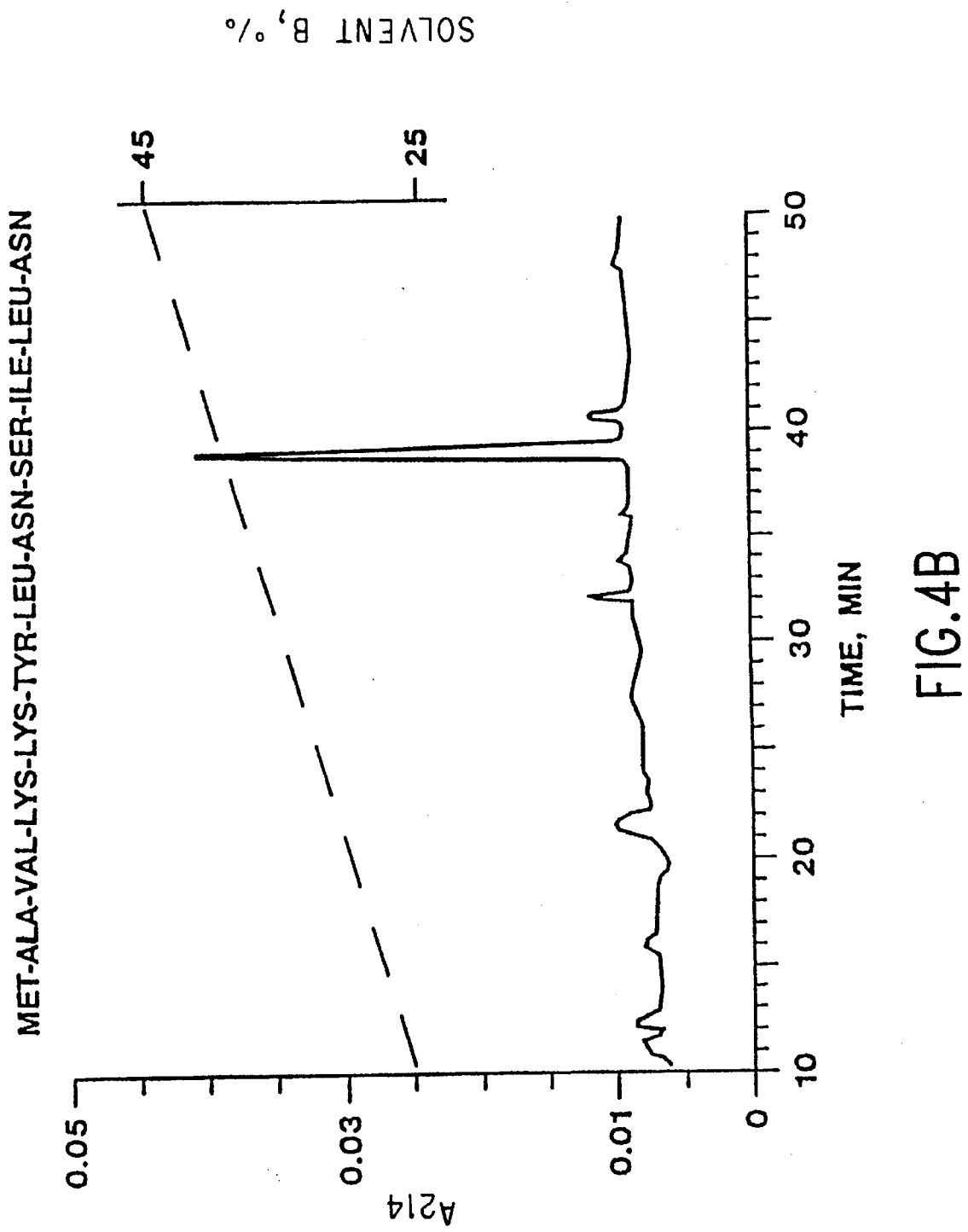

FIGS. 4A and 4B. Identification of VIP fragments produced by IgG, illustrating cleavage at the Gln-Met bond; and comparing catalytic IgG and non-catalytic IgG. VIP was treated with immune or nonimmune IgG, extracted on C-18 cartridges and subjected to reverse phase HPLC. Most of the $A_{124}$ absorbing material seen after treatment of VIP with the antibody was in a peak with retention time similar to that of intact VIP (21.3 min). Peptides A and B were missing after treatment in buffer or nonimmune IgG. These peptides were purified by rechromatography, (4A and 4B) respectively) and identified by amino acid sequencing.

FIG. 4A. HIS-SER-ASP-ALA-VAL-PHE-THR-ASP-ASN-TYR-THR-ARG-LEU-ARG-LYS-GLN.

FIG. 4B. MET-ALA-VAL-LYS-LYS-TYR-LEU-ASB-SER-ILE-LEU-ASN.

Figure 5A:
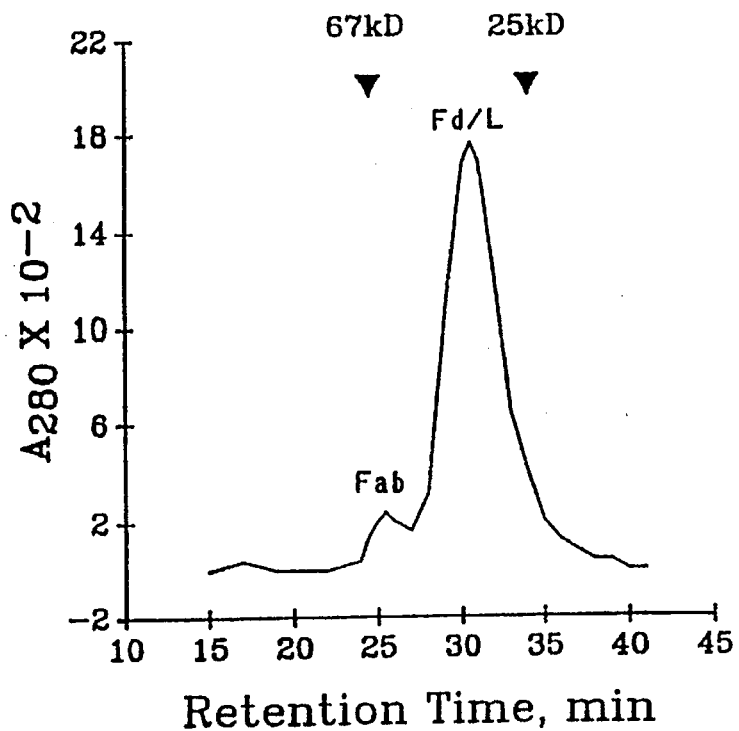
FIGS. 5A–5C. Demonstration of disaggregation to produce Fd.- and L-chains.
Figure 5B:
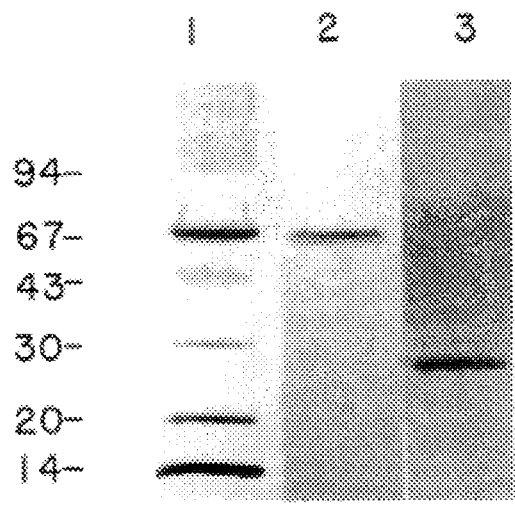
Figure 5C:
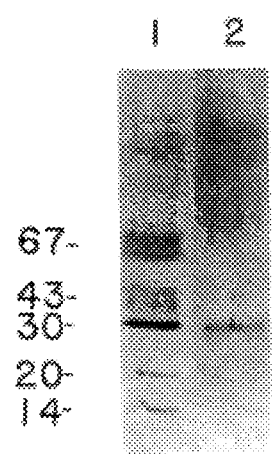

FIGS. 5A–5C. Demonstration of disaggregation to produce Fd- and L-chains.

FIG. 5A. Separation of reduced, alkylated antibody single chains. Gel filtration profile (Superose 12) of reduced, alkylated Feb. A minor early eluting peak and a major peak (retention time 31 min) are evident.

FIG. 5B. SDS-PAGE and silver staining revealed a 59 kD band in minor peak (lane 2) and a 24kD band in the major peak (lane 3). SDS produces disaggregation, thus it is necessary to run sample under native conditions as in 5(C) below to demonstrate that the disaggregation is due to prior treatment of the sample.

FIG. 5C. Native PAGE (without disaggregation induced by the separation technique) of the reduced, alkylated Fd-, L-chain mixture (lane 2) and marker proteins (lane 1). Demonstrates that the prior reduction and alkylation resulted in the separation of the Fd- and L-chains.

Figure 6:
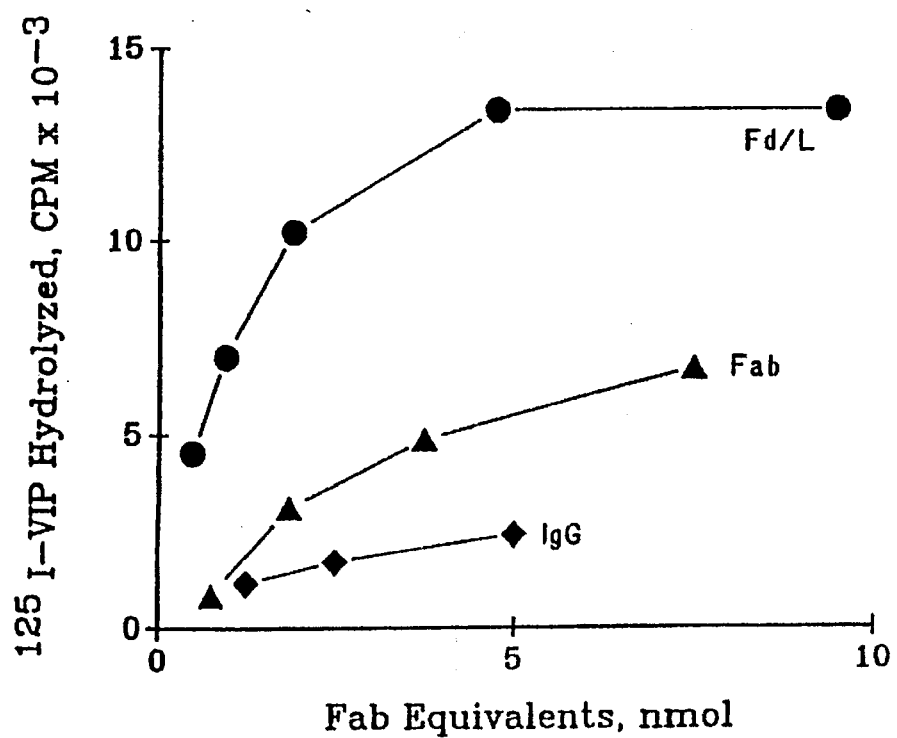
FIG. 6. VIP hydrolysis by intact IgG, Fab and antibody single chains, as a function of increasing IgG, Fab and Fd/L25 concentrations, showing that progressive dissection of the antibody resulted in increased hydrolytic activity.

FIG. 6. VIP hydrolysis by intact IgG, Feb and antibody single chains, as a function of increasing IgG, Fab and Fd-/L25 concentrations, showing that progressive dissection of the antibody resulted in increased hydrolytic activity. This data supports the concept that catalytic components may be produced from non-catalytic antibodies by progressive dissection.

FIGS. 7A–7D. Fortuitous preparation of catalytic dissociated L-chains of VIP-specific antibodies.

Figure 7A:
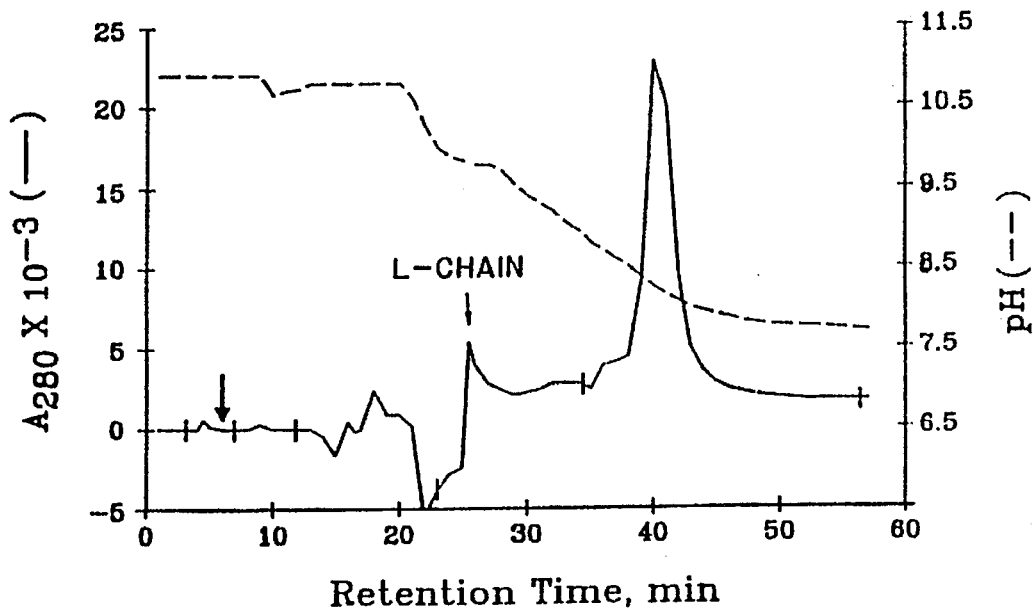
FIGS. 7A–7B Fortuitous preparation of catalytic dissociated L-chains of VIP-specific antibodies.

FIG. 7A. Purification of VIP antibody L-chains.

Figure 7D:
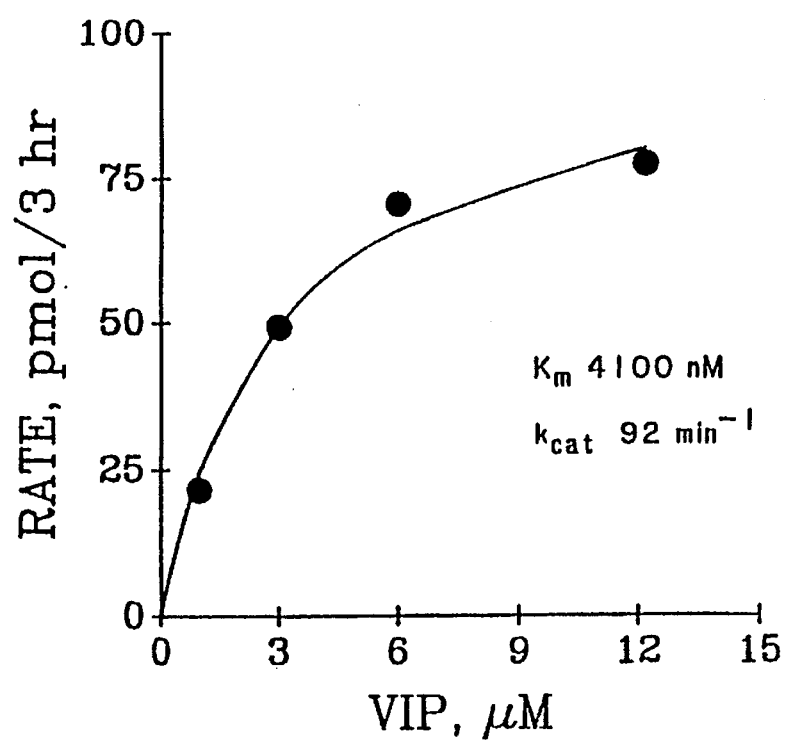
Figure 7B:
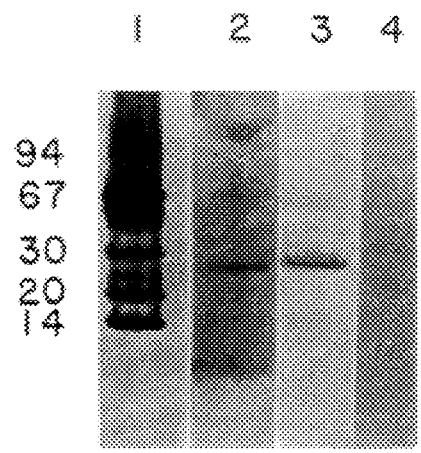

FIG. 7B. Reducing SDS-PAGE of the protein peak purified by chromatofocusing. (retention time 26 min.) stained with silver (lane 2), anti-L-chain antibody (lane 3) and anti-H-chain antibody (lane 4). Lane 1 shows silver stained marker proteins. Note lack of stain with anti-H-chain antibody.

Figure 7C:
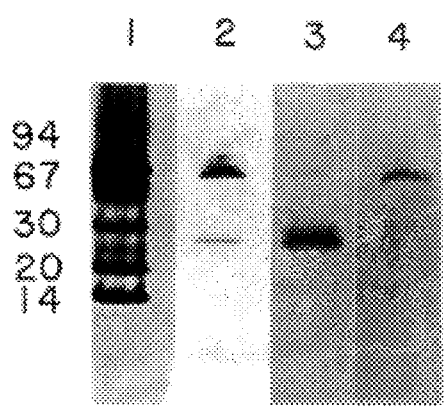

FIG. 7C. Reducing SDS-PAGE of a control intact IgG preparation (affinity purified antibody from subject 80). Land identities are as in (B).

FIG. 7D. VIP hydrolysis by purified antibody L-chains. Saturation kinetics of VIP hydrolysis by purified L-chains of VIP-autoantibodies (4 ng per assay tube). Data are fitted to the Michaelis-Menten equation.

Figure 8:
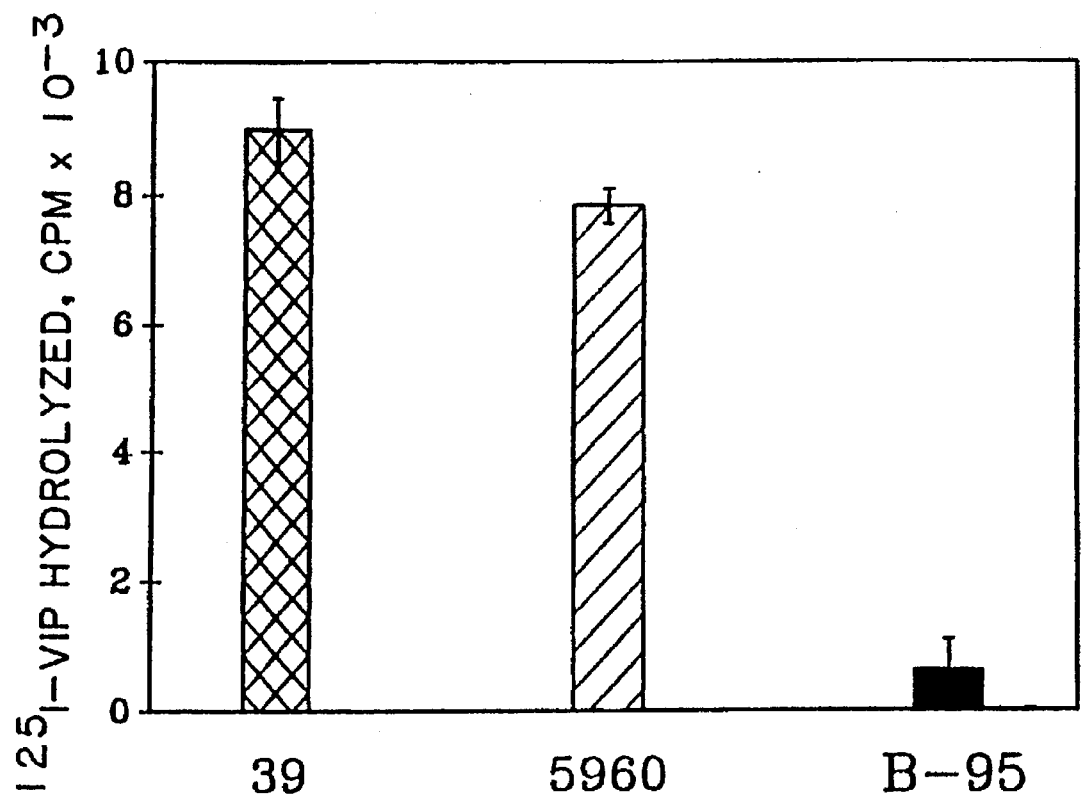
FIG. 8. VIP hydrolytic antibody synthesis by cultured EBV transformed lymphocytes. line.

FIG. 8. VIP hydrolytic antibody synthesis by cultured EBV transformed lymphocytes.

Figure 9:
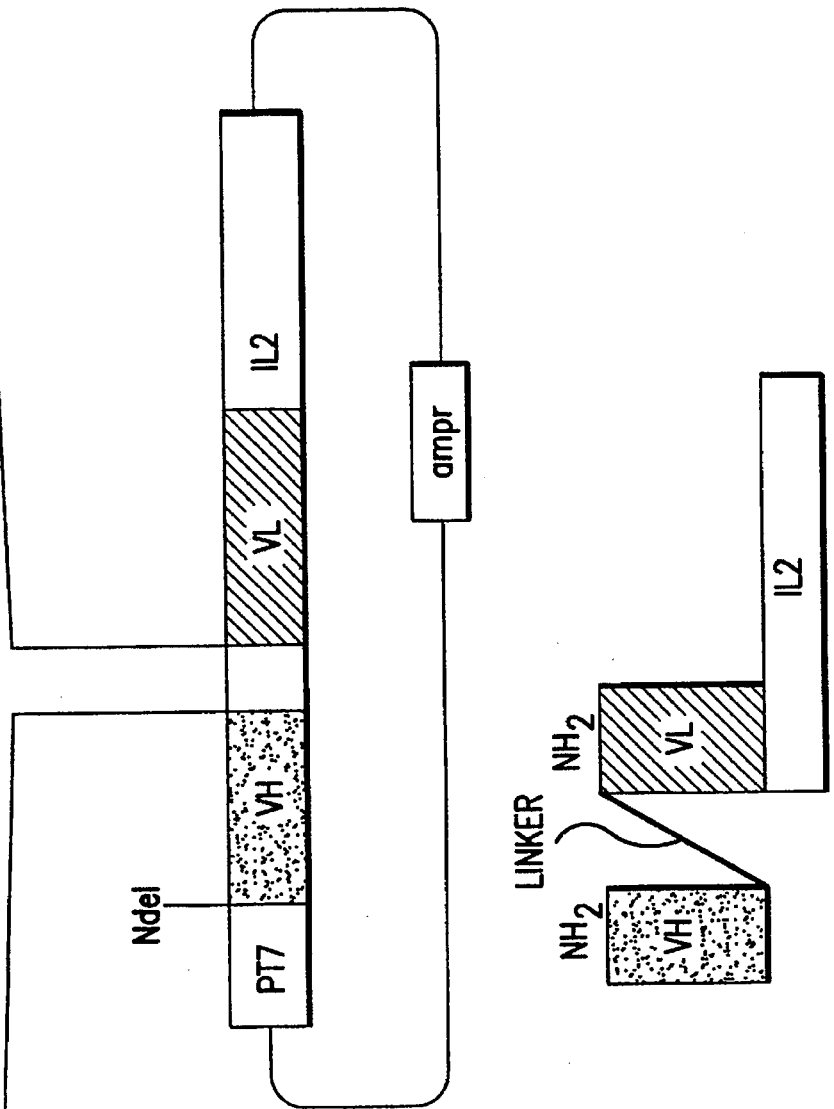
FIG. 9. Expression plasmid for Fv-Il -2 fusion protein and diagram of expression fusion protein.

FIG. 9. Expression plasmid for Fv-II-2 fusion protein and diagram of expression fusion protein. To create a single-chain recombinant plasmid is assembled (40) employing a DNA segment derived from a catalytic mAB, encoding the $V_H$ joined to a DNA segment encoding the $V_L$ by a 45-bp liner; $V_L$ was in turn joined to a DNA segment encoding interleukin-2 as shown. The assembled gene is under the control of the T7 promoter.

Figure 10:
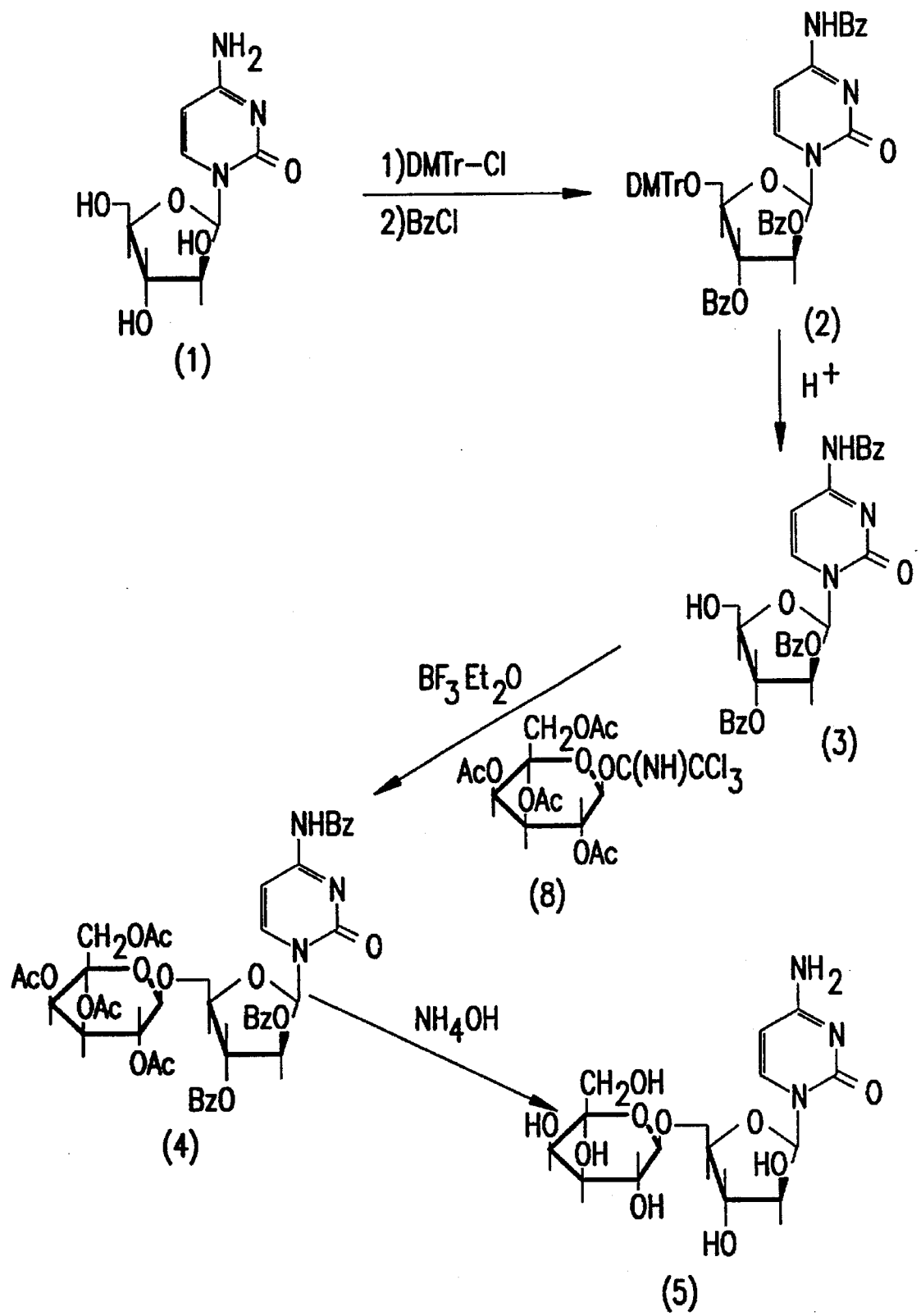
FIGS. 10–12. Chemical reaction pathways for production of pro-ARA-C.
Figure 11:
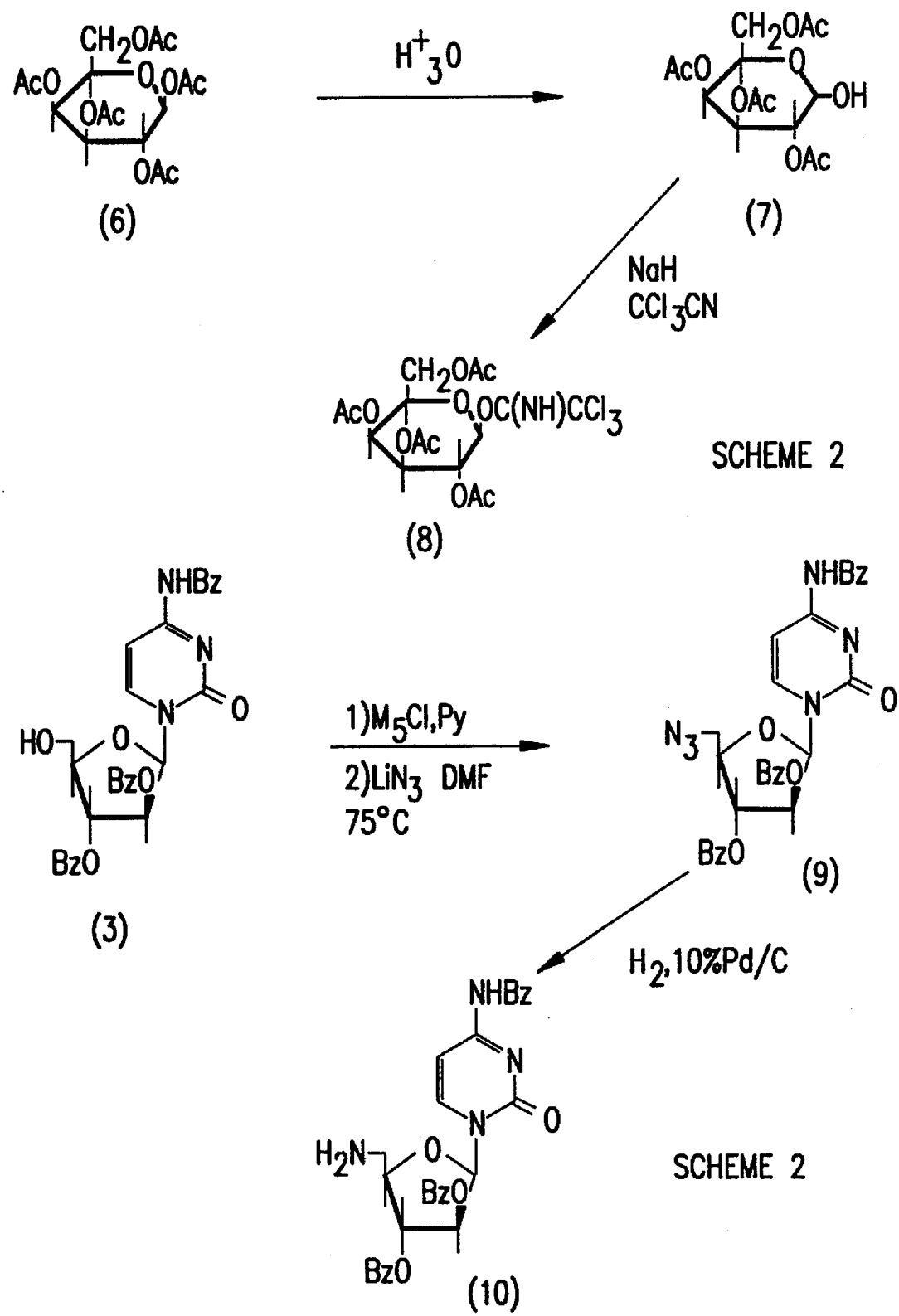
Figure 12:
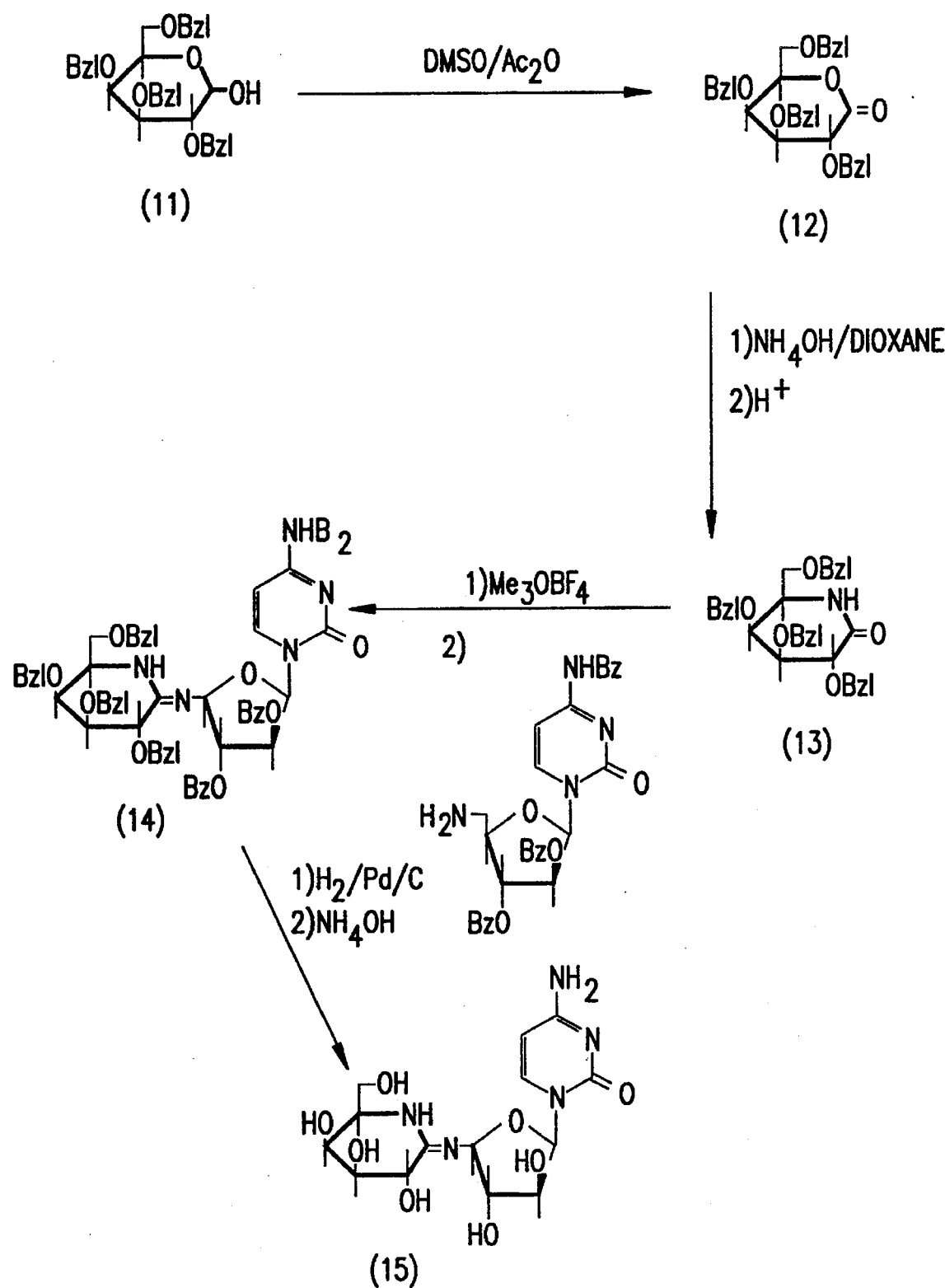

FIGS. 10–12. Chemical reaction pathways schemes 1, 2, and 3 for production of pro ARA-C.

Specific Embodiments

Several different components of antibodies are capable of catalyzing a chemical reaction. The components may be catalytic components of antibodies, which antibodies themselves have catalytic activity for a given reaction, or, the catalytic components may be components of antibodies which themselves do not exhibit catalytic properties.

The several catalytic component parts include the Fab portion of an antibody, the Fd fragment of an H-chain, the Fv portion of an antibody, an L-chain, an H-chain, a mixture of an L- and H-chain wherein the chains are present as unassociated, i.e. free monomers, dimers which may be either heterodimers or homodimers, a variable fragment of an L-chain, a variable fragment of an H-chain, a catalytic domain of an L-chain, and a catalytic domain of an H-chain. The Fv and Fab components, as noted above, are not known for the promotion of cleavage or formation of peptide bonds, but are known for catalysis of less energetically demanding reactions such as amide or ester hydrolysis.

It has now been shown that the catalytic activity of an antibody able to promote the cleavage or formation of peptide bonds is found to be present in, in addition to the IgG, in the Fab component thereof and also in a preparation of dissociated H- and L-chains, each having a molecular mass of 25 kD. The IgG, the Fab, and the dissociated Fd and L-chains each catalytically hydrolyzed vasoactive intestinal peptide (VIP).

The several catalytic components of the antibody or catalytic antibody may be obtained by different methods.

Catalytic properties of the several components may, on the one hand be present in an original antibody or catalytic antibody and be retained during the fragmentation process or, on the other hand these properties may be created by the process of producing the component. The process of producing antibody components which are unconstrained by the complete structure of a physiologic antibody can yield a component with a catalytic property, for example, in a component produced directly or indirectly (by recombinant methods) from a non-catalytic antibody.

Catalytic Autoantibodies

A catalytic component of a catalytic autoantibody can be prepared by first identifying an animal with an autoantibody to a self-antigen of the animal, isolating a serum fraction containing a plurality of antibodies, screening the serum fraction to identify an autoantibody which enhances the rate of a chemical reaction important to an autoimmune disease process, and obtaining a catalytic component of the autoantibody.

An animal with autoantibodies to a self-antigen of the animal is identified by measuring, in plasma samples or purified IgG from the animal, the saturable binding of the autoantibodies to the self-antigen of the animal itself, to a self-antigen of a different animal species which is identical or substantially identical to the self-antigen of the animal or to a synthetic self-antigen which is identical or substantially identical to the self-antigen of the animal, using methods well known in the art. A catalytic autoantibody is identified by screening autoantibodies for those which promote the catalytic cleavage or formation of a chemical bond of interest. Candidate autoantibodies are contacted with a self-antigen of the animal itself or to a self-antigen of a different animal species which is identical or substantially identical to the self-antigen of the animal, and the products of cleavage or formation of chemical bonds of interest of that self-antigen, or substantially identical antigen, are detected by methods well known to the art.

In another embodiment of the invention, the isolated autoantibodies are purified by standard methods and then ultrafiltered. The term "ultrafiltration" as used herein refers to a filtering process employing a membrane having pores with an average cut off molecular weight ranging from 1,000 to 10,000 Daltons. Thus, for example, ultrafiltering an immunoglobulin with a molecular weight of 150,000 Daltons on a membrane with pores having an average cut off molecular weight of 10,000 Daltons will cause molecules with molecular weights smaller than 10,000 Daltons to pass through the membrane while the immunoglobulin will remain on the membrane. This process activates the antibody catalytic property and a small molecular weight inhibitor may be purified from the ultrafiltrate.

The isolated autoantibodies are then screened for rate enhancement activity. Screening can be conveniently accomplished by treating a standardized solution of the reactant/substrate with an aliquot of medium containing the autoantibodies and measuring the presence of the desired product by conventional instrumental methods. This measurement can be readily conducted, for example; by spectrophotometric methods or by gas-liquid or high pressure liquid chromatography. By comparison with standardized samples of the desired product or reactant/substrate, rates of reaction can be quantified.

Rationally Designed Antibodies

A catalytic component of a rationally designed catalytic antibody may be obtained starting with the methods taught in U.S. Pat. Ser. No. 4,888,281. According to such processes, a plurality of monoclonal antibodies is prepared to an antigen selected from the group consisting of (i) the reactant, (ii) the reactant bound to a peptide or other carrier molecule, (iii) a reaction intermediate, (iv) an analog of the reactant, (v) an analog of the product in which the monoclonal antibody so generated is capable of binding to the reactant or a reaction intermediate, or (vi) an analog of a reaction intermediate. The plurality of monoclonal antibodies so generated is screened to identify a monoclonal antibody which catalyzes the reaction of interest and the monoclonal antibody which is desired to have the desired catalytic activity separated into its several components and those components screened for activity such that a catalytic component is obtained.

In still a further and related process, an animal is immunized with an antigen selected from the group consisting of (i) the reactant, (ii) the reactant bound to a peptide or other carrier molecule, (iii) a reaction intermediate, (iv) an analog of the reactant, (v) an analog of the product in which the monoclonal antibody so generated is capable of binding to the reactant or a reaction intermediate, or (vi) an analog of a reaction intermediate, thereby generating antibody-producing lymphocytes in said animal, antibody-producing lymphocytes are removed from the animal, those lymphocytes are fused with myeloma cells to produce a plurality of hybridoma cells each of which produces monoclonal antibodies, the plurality of monoclonal antibodies is screened to identify a monoclonal antibody which catalyzes the reaction, and, a catalytic component of that monoclonal antibody is obtained as further described below.

In yet a further related method, a catalytic antibody for a chemical reaction which is known to be catalyzed by an enzyme can be first obtained and then its components screened to identify and obtain the catalytic component. In this process, a plurality of monoclonal antibodies is produced to the enzyme, that plurality of monoclonal antibodies is screened to identify a monoclonal antibody which inhibits binding of the reactant to the enzyme, and that first monoclonal antibody is recovered. Thereafter, a further plurality of anti-idiotype monoclonal antibodies to the first antibody is generated, these are screened to identify a second monoclonal antibody which binds the reactant and catalytically increases the rate of reaction, and that monoclonal antibody is reduced to its component parts which are screened to obtain a catalytic component of the monoclonal antibody.

In each of the above-described methods, if the catalytic component is known, the screening of the components may be omitted and the desired catalytic component of the antibody may be directly obtained.

Where the catalytic component part is an L- or H-chain of a catalytic antibody, the chain may be prepared by a process wherein catalytic antibody is purified and then cleaved into Fab and Fc fractions. The Fab fraction is then reduced and alkylated to cleave bonds connecting the L- and H-chains, and the L- and H-chains are separated.

Where the catalytic component part is a single chain of a catalytic antibody, the chain may be prepared by dissociating the catalytic antibody into its component L- and H-chains and then separating those L- and H-chains. Separation may be achieved by passing the antibody through a column which is selective for molecular weight or charge. A certain percentage of the antibody protein chains spontaneously dissociate during this process and appear as separate single chain peaks. This appears to be facilitated by separation after diluting the antibody to a concentration of less than 5 µg/ml in detergent at alkaline pH.

Alternatively, L- and H-chains may be dissociated by a process wherein the antibody is reduced with a reducing agent selected from the group consisting of mercaptoethanol, dithiothreitol, and mercaptethylamine and thereafter the SH groups on the reduced antibody are alkylated with an alkylation agent selected from the group consisting of iodoacetamide and iodoacetic acid.

In still a further method for obtaining catalytic component parts of catalytic antibodies, an L-chain or H-chain Fd fragment thereof may be prepared by purifying the catalytic antibody, cleaving the purified antibody into Fab and Fc fractions, reducing and then alkylating the Fab fraction to cleave bonds connecting the L-chain and H-chain Fd fragment, contacting the L-chain and H-chain Fd fragment with a ligand or other binding molecule capable of binding to one or the other of said L- or H-chains under conditions conducive to binding, and, separating the bound L-chain or bound H-chain Fd fragment from the unbound components.

The catalytic component part may be a catalytic domain comprising a polypeptide which is a part of a variable region of a catalytic antibody or of an H- or L-chain thereof and which retains the catalytic activity. The catalytic component part may be replicated by expressing in a non-hybridoma cell a nucleic acid genetic sequence copied from the catalytic component part. For example, the component part may be replicated by inserting into a cell a fragment of a gene coding for said component part.

Alternatively, the catalytic component part may be a catalytic domain which is prepared by cleaving the variable region of the catalytic antibody into a series of peptide sequences, screening those peptide sequences to identify a peptide sequence having catalytic activity, and thereafter purifying the so-identified catalytic domain. In a preferred embodiment, the catalytic domain may be prepared in a process which includes the additional steps of cleaving the peptide sequences to generate increasingly smaller peptide sequences and screening those cleaved sequences to identify those having catalytic activity. This step may then be repeated until no catalytic activity is detected in the cleavage products. The identified catalytic domain can then be purified. Once the catalytic domain is identified by determination of the peptide sequence thereof, copies may be synthesized.

The catalytic domain may also be prepared by determining the peptide sequence of the $V_L$ or $V_H$ of the catalytic antibody, then synthesizing an overlapping series of homologous peptides representing sections of the peptide sequence of the variable region, screening the series of overlapping homologous peptides to select those with desirable catalytic properties and synthesizing the selected peptide sequence. A similar result may be achieved by determining the nucleic acid sequence of the $V_L$ or $V_H$ of the catalytic antibody, cleaving the nucleic acid sequence into fragments or synthesizing overlapping oligonucleic acid subsequences, and then expressing these $V_L$ or $V_H$ subsequences in a cell line by known methods. The resulting series of subsequence peptides may then be screened for desirable catalytic properties as described above.

In still another method, the catalytic domain may be prepared by determining the sequence of the variable region of the catalytic antibody, inserting into any cell (prokaryotic or eukaryotic) a gene coding for the variable region of the catalytic antibody, and, expressing the variable region in the cell. The inserted gene may code for a fragment of the variable region. The cell may be an animal cell, e.g. a mammalian cell, a plant cell, or a microorganism, e.g., bacteria, yeast, mold, protozoa, and fungi. If desired, the gene may be subjected to mutagenesis before or after insertion into the cell.

In still a further method of the invention, the catalytic component part of the catalytic antibody may be produced by a process which includes inserting into any cell (prokaryotic or eukaryotic) at least one nucleic acid sequence coding for a variable region of the antibody, subjecting the nucleic acid sequence to mutagenesis before or after such insertion, screening the cell and its progeny for the presence of mutated variable regions of the antibody which demonstrate desired catalytic activity, replicating the cell, and, expressing the mutated nucleic acid sequence to produce a translation product with the desired catalytic activity.

In an additional process a population of cells producing antibodies, e.g. hybridomas, may be selected for those cells producing component parts of antibodies such as L- and H-chains in place of all or part of the production of intact physiological antibodies.

The catalytic components of the invention may be usefully combined with or associated with one another or to molecules having other, non-catalytic, chemical, biological, or mechanical functions. The association may be non-covalent (e.g. hydrogen bonding or charge interaction or related types of association). The association may also be covalent, utilizing any of the methods well known to the art to link the components to one another or to other molecules while retaining the desired functions of the components and the linked molecules.

Chimeric products may be prepared by expressing nucleic acid sequences coding for a continuous polypeptide sequence which contains a catalytic antibody component part and at least one other protein. The nucleic acid sequence thus may comprise a first nucleic acid sequence coding for a catalytic component part of an antibody, and, at least one additional nucleic acid sequence coding for either the same catalytic component part, a different catalytic component part, or at least one additional protein having a biological function different from that of the catalytic component part. The additional protein may be a biological binding protein such as a ligand, for example, avidin, streptavidin, protein A, and protein G. The additional protein may be an H-chain or L-chain of an antibody able to bind to an antigen of interest. Alternatively, the additional protein may be the variable region of an antibody able to bind to an antigen of interest.

Cells may be created which express and secrete, in vivo, catalytic components, proteins or peptides according to the invention for therapeutic, diagnostic or industrial purposes. Cells may be taken from an animal or plant, genetically engineered to express (the protein may be designed by known methods to remain within the cell, to remain on the cell surface or to be secreted from the cell) desirable catalytic components or chimeric proteins embodying one or more components, and then the cell may be reintroduced into the animal or plant where the catalytic component will serve a desirable function e.g. a therapeutic, metabolic, immunological, or diagnostic function.

The invention is further described in the following examples.

EXAMPLE I

Purification of VIP Specific Catalytic
Autoantibodies From Human Blood By Affinity
Chromatography The IgG fractions containing VIP hydrolytic autoantibodies exhibit relatively tight binding of VIP. This property may be used to purify specific catalytic autoantibodies on a VIP-Sepharose column. Synthetic VIP (10 mg) mixed with about 20,000 cpm (Tyr$^{10}$–$^{125}$I)-VIP was covalently coupled to 5 g CNBr-Sepharose according to the manufacturers instruction (16). Coupling efficiency was approximately 90%, judged by the amount of radioactivity that was immobilized. The VIP-Sepharose (4.5 ml gel) was incubated with 15 mg IgG in 3.5 ml 100 mM glycine, 50 mM Tris-HCL, pH 8.0 for 2 h at 4° C. The mixture was poured into a column, the gel washed with buffer until the A$_{280}$ returned to baseline, bound IgG eluted with 0.1M glycine-HCl, pH 2.7 and neutralized with 1M Tris-HCl, pH 9.0. Analytical isoelectric focusing of this antibody preparation on PHAST gels (pH gradient 3–10) followed by silver staining revealed a series of closely spaced bands with pI 6.5 to 8.5. SDS-gel electrophoresis under reducing conditions (5% mercaptoethanol) followed by silver staining and immunoblotting revealed that the antibody was composed of subunits corresponding to a 50 kD H-chain and a 25 kD L-chain. The affinity purified antibodies were incubated with 210 pg (Tyr$^{10}$–$^{125}$I)-VIP for 3 h at 38° C., the reaction mixture extracted on a Seppak C-18 cartridge and subjected to reverse phase HPLC (FIG. 2). An early eluting peak of radioactivity was noted (retention time 10 min), distinct from intact $^{125}$I-labeled VIP (retention time 21.0 min). This early eluting peak of radioactivity had a retention time identical to that of synthetic VIP(1–16) labeled with $^{125}$I. It has previously been shown that the unfractionated IgG cleaves VIP at the peptide bond between residues 16 and 17 (17). Data shown here indicated that the affinity purified material cleaves VIP at the same bond (Gln$^{16}$-Met$^{17}$) (FIGS. 4A–4B).

EXAMPLE II

VIP Hydrolysis by Purified Autoantibody

A. Preparation of $^{125}$I-labeled VIP Substrate.

The (Tyr$^{10}$–$^{125}$I )-VIP was prepared by known methods (29,1). Iodination of purified porcine VIP was by the chloramine T method in a sodium phosphate buffer. Following preliminary fractionation on a C18 cartridge, the reaction mixture was purified further by reverse phase HPLC on a Novapak C18 column using a gradient of trifluoroacetic acid in acetonitrile for elution. Two well defined peaks of radioactivity were consistently obtained that were reactive with rabbit anti-VIP antiserum in radioimmunoassay. Amino acid sequencing has shown that the early eluting peak of radioactivity (retention time 25.3 min) corresponds to (Tyr$^{10}$–$^{125}$I)VIP and the second peak of radioactivity (retention time 27.8 min) corresponds to di(Tyr$^{10}$–$^{125}$I)VIP, Tyr$^{22}$)VIP (FIG. 2). The monoiodinated form of the peptide was preferred because it most closely corresponds in structure to unlabeled VIP.

B. Hydrolysis of $^{125}$I-labeled VIP Substrate.

To evaluate the kinetics of VIP hydrolysis, 66.3 ng purified antibody was incubated with increasing concentrations of VIP in the presence of approximately 30 pM (Tyr$^{10}$–$^{125}$I)-VIP. The reaction was terminated with 10% trichloroacetic acid, a procedure that precipitated undegraded VIP and left the radioactive fragment (VIP 1–16) produced by antibody mediated hydrolysis in the supernatant. A plot of the reciprocals of the rate of VIP hydrolysis and the VIP concentration was linear, suggesting conformity with Michaelis-Menton kinetics. K$_m$ and k$_{cat}$ calculated from these data using the program ENZFITTER (Elsevier) were 110.4 nM and 0.11 min$^{-1}$.

Previous studies have indicated multiple turnovers of the autoantibody, based on the assumption that the autoantibodies detected in VIP binding studies were responsible for hydrolysis of the peptide (17). Data shown here provide direct evidence for efficient catalysis by the autoantibodies.

EXAMPLE III

Hydrolysis of VIP by IgG (Test Tube Assay)

A standard protocol to measure presence of hydrolysis.

Final assay volume was set at 200 µl but the volume of each component may vary depending on purpose of the assay.

All dilutions were made in degradation buffer (0.1M glycine-HCl, 50 mM TRIS-HCl pH 8.0 with 0.025% Tween). Sample IgG was typically be diluted to 1 mg/ml and 0.5 mg/ml starting concentration for the initial test. VIP specific antibody was be used at lower concentrations (approximately 1 µg/ml).

$^{125}$I-VIP was diluted to 15,000 cpm per 50 µl.

BSA (4% stock) was diluted to give a final assay concentration of 0.1%. Usually, 100 µl of 0.2% BSA was added to the assay.

Assay tubes contained 100 µl 10.2% BSA, 50 µl $^{125}$-VIP (15,000 cpm) and 50 µl IgG sample. One set of tubes with buffer in the place of antibody was set aside as a control.

All tubes were capped and vortexed after all components are added.

Incubation was for 3 hr at 38° C. in the shaking water bath. Each tube was uncapped and 1 ml cold 12% TCA added to all tubes except TC and vortex.

Centrifugation was at 5800 rpm for 20 min. All tubes but the TC tube were aspirated. The pellets were counted in a gamma-counter (FIGS. 4A–4B).

EXAMPLE IV

Protein G-Sepharose, Purification of IgG from Plasma

The Protein G-Sepharose (Pharmacia) was washed with water on a sintered glass funnel (#36060, Pyrex) or in a column. At least 3 ml water per ml gel was used for each wash. The gel was suspended at least 3 times on sintered glass funnel or in column. The gel was then resuspended in 0.05 m TRIS-HCl pH 7.3 (start buffer) and packed into a column of appropriate size (or allow to pack if using column that has been poured). One ml Protein G-Sepharose was used for each 1 ml human plasma. The column was then equilibrated with 2–3 column volumes of start buffer and run at 0.4 ml/min for 0.7 cm diameter column or 0.8 ml/min for 1 cm diameter column. The sample was centrifuged (5,000 rpm, 10 min) and filtered on Millex-GS filter (0.22 µM) and applied to the column (dialyzed ammonium sulfate precipitate of plasma) and run into the gel bed. The start buffer was added and run until A$_{280}$ returns to baseline. (In the event that no peak was observed approximately 15 ml of start buffer was run.)

The buffer was then changed to 0.1M glycine—HCl, pH 2.7 and eluted to the same flow rate. Fractions (1 ml) were collected into tubes containing 50 µl 1M TRIS-HCl, pH 9 to minimize acid induced denaturation (this brings pH to 7.8.). The column was re-equilibrated (2 column volumes) to start buffer and stored in 20% ethanol at 45° C.

EXAMPLE V

Purification Of Catalytic Chains Of VIP Autoantibodies

The IgG from a human subject (code #39) was subjected to affinity chromatography on VIP-Sepharose. The affinity purified antibodies were then chromatographed on a mono-P column in three steps (18). The pH gradients used in these three chromatofocusing steps were 7.0 to 4.0, 9.0 to 6.0, and, finally, 10.5 to 7.0. The VIP hydrolytic antibody was recovered in the nonretained fraction during the first two chromatofocusing steps. In the third chromatofocusing step, a protein eluting between pH 8.3 and 7.8 possessed VIP hydrolytic activity (FIG. 7A). Analytical isoelectric focusing followed by silver staining revealed a single protein band with pI 9.6 in this preparation. SDS-PAGE (non-reducing) revealed two protein bands. The major band had a molecular mass of 25 kD and was stainable with anti-human L-chain antiserum in immunoblots. The minor band had a mass of 55 kD and was also stainable with anti-L chain antiserum, suggesting that it is a L-chain dimer. These data suggest that this preparation is composed primarily of L-chains derived from VIP-autoantibodies. An alternative method of SDS electrophoresis provided similar results. Purification of IgG antibody electrophoresed under reducing conditions exhibited a 26 kD anti-L-chain stained band and a 61 kD anti-H chain stained band (FIG. 7B).

The data supports the conclusion that the chromatofocused preparation was composed of L-chains free of detectable H-chain contamination. This L-chain fraction hydrolyzed VIP with $k_{cat}$ 92.4 min$^{-1}$ and $K_m$ 4.9 µM (FIG. 7D). The $K_m$ value for the L-chain is about 45-fold larger than that of the starting IgG, suggesting decreased binding affinity.

EXAMPLE VI

VIP Hydrolysis by Purified L-Chain

To evaluate the kinetics of VIP hydrolysis, about 3.7 ng purified L chains were incubated with increasing concentrations of unlabeled VIP in the presence of approximately 30 pM (Tyr$^{10}$-$^{125}$I)-VIP. The reaction was terminated with 10% trichloracetic acid, a procedure that precipitated undegraded VIP and left the radioactive fragment of hydrolyzed VIP in the supernatant. A plot of the reciprocals of the rate of VIP hydrolysis and VIP concentration was linear, suggesting conformity with Michaelis-Menton kinetics. $K_m$ and $k_{cat}$ calculated from these data using the program ENZFITTER (Elsevier) were 4.9 µM and 40.6 min.$^{-1}$.

It is likely that the L-chains isolated arose by the spontaneous reduction of disulfide bonds between the H and the L chains as a result of manipulating of the antibody preparation at very dilute concentrations (less than 5 µg/ml) and exposure of the antibody preparation to extreme pH values (up to pH 10.5). The data clearly shows that the dissociated L-chain of the VIP autoantibody possesses catalytic activity.

EXAMPLE VII

Treatment of

With Immobilized Papain (Fab Production) Cysteine (Sigma) was added to 20 mM in 20 mM NaH$_2$PO$_4$ with 10 mM EDTA pH 7.0, to make digestion buffer. The immobilized papain agarose gel (Pierce)(0.5 ml, equivalent to 0.25 ml settled gel volume) slurry was then added to a 13×100 mM glass tube. Then, 0.75 ml settled gel was used to digest 7.5 mg IgG. Four ml of digestion buffer was then added and mixed. This mix was centrifuged at 1000 rpm for 5 min. The buffer was discarded and the procedure repeated. The papain gel was resuspended in 0.5 ml digestion buffer and transferred to a 25 ml flask. IgG (up to 10 mg IgG, usually 2–7.5 mg to papain gel was added. Digestion buffer was added to make 1.5 ml total incubation volume.

Incubation was at 38° C. with shaking (top speed of shaking water bath) for 5 h or overnight. Following incubation 1.5 ml 10 mM TRIS-HCl pH 7.5 was added and the gel and solution was transferred back to a 13×100 mM glass test tube. This was centrifuged at 1000 rpm for 5 min.

The supernatant was then applied to equilibrated Protein A agarose column (2.5 ml gel for up to 20 mg papain digested IgG). Fab was separated from residual intact IgG on a Protein A agarose column. Protein A column purification was run the same way as the Protein G-Sepharose column of Example IV, except that the start buffer is 10 mM TRIS-HCl pH 7.5, and column is regenerated with 0.1M citric acid, pH 3 and storage is in 0.2% sodium azide. The papain digested material was applied to the column (previously equilibrated with the chromatography buffer). The nonretained portion was tested for purity of Fab by electrophoresis (FIG. 3A). Retained portion was a mixture of nondigested IgG, Fc fragment and other fragments with an Fc portion.

The Fab was able to catalytically hydrolyze $^{125}$I-labeled VIP using the method of Example VI (FIG. 3B).

EXAMPLE VIII preparation of Dissociated Mixture of Heavy and Light Chains (Fd/L 25 kD)

To about 2 mg Fab (Example VII), Nacl was added to 0.15M, and mercaptoethanol was added to 0.2M in a final volume of 5 ml of 50 mM Tris-HCl, pH 7.3. This mixture was incubated at 24 C. for 3 h with shaking. Then 2 ml of 0.5M iodoacetamide was added, followed by the addition of 1M Tris.HCl (900 µl) to bring pH to 7.5. This mixture was incubated for 15 min at 24 C. with shaking. The sample was then concentrated to reduce the volume to about 1 ml on a 10 kD ultrafilter (YM10).

The resulting concentrated sample was chromatographed on Superose-12 in buffer (0.1M glycine-HCL, 0.05M Tris-HCL, pH 8.0 containing 0.025% Tween 20). The protein peaks from the Superose-12 were analyzed by SDS-PAGE (FIG. 5B). Pooled functions showed a molecular mass of 25–30 kD in the SDS-PAGE analysis. This is the Fd/L25 fraction. Note that the minor peak seen in lane 2 of FIG. 5C is undissociated Fab and the major peak is unassociated 25 kD Fd/L. The Fd/L-chain mixture was able to catalyze the cleavage of VIP as illustrated in (FIG. 6).

EXAMPLE IX

Separation of Dissociated Mixture of Heavy and Light Chains Into Purified Fd- and L-Chains The unassociated L-chain/Fd- mixture resulting from Example VIII is subjected to further separation procedures in order to fractionate dissociated Fd, dissociated L-chains, and dimers. The first such separation procedure consists of chromatofocusing on a Mono-P column using pH gradients of 10.5–7.0, 9.0–6.0 or 7.0–4.0, as appropriate. Optical absorbance (280 nm) and pH of the effluent is monitored. VIP hydrolyric activity is assayed in the protein peaks. Protein peaks with VIP catalytic activity are collected for further analysis. The peaks with VIP catalytic activity have molecular weights of about 25–26 kD and about 50–60 kD. The identity of the proteins is ascertained by SDS-gel electrophoresis on Phast gels (Pharmacia, 8–25%) followed by silver staining and immunoblotting.

A. Standardized Immunoblotting Procedure

The following standard method is used to detect Fd, H- L-chain and other components of antibodies with high sensitivity. Gels are blotted on nitrocellulose membranes, the membranes incubated in anti-human L-chain (kappa/lambda) or anti-H chain antibodies (Accurate), washed with buffer, incubated with anti-rabbit IgG conjugated with peroxidase, washed, and then stained with diaminobenzidine and $H_2O_2$.

D. Immunoblotting Interpretation

Staining of the 26 kD bands with anti-L chain and anti-H chain antibodies indicates the presence of L-chains and Fd-, respectively. Staining of the 26 kD band with one type of antiserum and not the other indicates that the preparation is composed of pure Fd- or L-chains. Staining of a 50–60 kD band represents homo- or heterodimers when these are present. Lack of staining of this band with one of the antisera in immunoblots indicates the absence of Fd-L heterodimers.

C. Affinity Chromatoqraphy Separation

In an alternative method, affinity chromatography is applied using specific anti-H (e.g. anti-Fd) or anti-L-chain antibodies immobilized on a solid support.

IgG from these antisera (or ascites fluid) are purified by chromatography on protein G-Sepharose and then coupled covalently (16) to CNBr-Sepharose (Pharmacia).

To fractionate dissociated Fd- and L-chains from the unassociated mixture, affinity chromatography using a column prepared with these immobilized antibodies is performed, using acid shock (pH 2.7) to elute the retained protein. Identity of the fractionated material is confirmed by immunoblotting for Fd- and L-chains as before. Native polyacrylamide gel electrophoresis and silver staining on PHAST gels is conducted to confirm that the purified Fd- and L-chain are monomeric (as for FIGS. 5A–5C). Since antibodies and antibody fragments can be very basic, reversed polarity electrodes are used for the native PAGE, when necessary.

EXAMPLE X

Catalysis by Antibodies and Single Chain Components

A. Kinetic properties

The catalytic properties and kinetics of intact Fab component and the purified, dissociated Fd component and L-chain derived from Example IX are determined. Antibody concentrations sufficient to yield hydrolysis of about 3,000 CPM are incubated with ($Tyr^{10-125}$) VIP in the presence of increasing concentrations of unlabeled VIP for 3 hours at 38° C. The amount of VIP hydrolyzed is calculated from the amount of radioactivity rendered soluble in 10% TCA by. the antibodies. To confirm that the TCA-precipitation method is a valid indicator of VIP hydrolysis, reverse phase HPLC of antibody treated ($Tyr^{10-125}$) VIP is performed. The decrease in the amount of radioactivity in intact ($Tyr^{10-125}$) VIP (retention time 25 minutes) is equivalent to the amount of radioactivity rendered TCA-soluble, when the antibody cleaves peptide bonds located between residues 7 and 22 of VIP. The data is analyzed by the program ENZFITTER (Elsevier) and plots of rate of hydrolysis versus the substrate concentration are constructed.

The reaction kinetics are first order with respect to substrate concentration. The data is fitted to the equation $V=V[S]/K_m+[S]$ where V is maximal reaction velocity, $K_m$ the VIP concentration at V/w, v the initial reaction velocity, and [S] the VIP concentration. $K_{cat}$ is obtained as [pmol VIP hydrolyzed per minute/pmol antibody or antibody single chains; normalized for valency (intact IgG=2; Fab=1, H- and L-chains=1) and molecular mass (Fab 60 kD; Fd- and L-chains, 25 kD)].

Catalytic efficiency is computed as $k_{cat}/K_m$. Increased $K_m$ values for the dissociated chains indicates decreased binding affinity. Increased $K_m$ values are not detrimental to the rate of catalysis so long as the binding step is not the rate limiting step.

B- Identification of The Peptide Bonds in VIP Cleaved by Catalytic Antibodies and Catalytic Single Chain Components In order to determine which VIP peptide bonds are cleaved by each component, a labeled VIP is cleaved by each of type of component tested. ($Tyr^{10-125,172}$)VIP (50 µg) or ($^{14}C$-His, $^{3}H$-$Asn^{28}$)VIP (50 µg) is treated with IgG, Fab, single Fd-chains and L-chains (a quantity sufficient to hydrolyze at least 5% of the peptide, based on kinetic analyses), non-immune IgG or assay diluent for 3–6 hours at 38° C. The reaction mixtures are extracted on C-18 cartridges (Alltech), the eluates dried in vacuo and then subjected to reverse phase HPLC on a Novapak-C18 column using a gradient of acetonitrile in trifluoroacetic acid. The absorbance of the eluate at 214 nm is monitored. $A_{124}$ absorbing, radioactive peptides are present in reaction mixtures of VIP treated with immune IgG, but absent in VIP treated with an equivalent quantity of non-immune IgG or assay diluent are pooled and purified further by a second round of reverse phase HPLC based on the elution behavior in the initial HPLC. Purified peptides are sequenced using an Applied Biosystems pulsed liquid phase sequenator with online PTH-amino acid detection. The cleaved bonds are identified by the size and identity of the cleavage fragments.

C. Determination of the Ability of Catalytic Antibodies and Single Chain Components to Cleave peptides Unrelated to VIP In order to determine the sequence specificity of cleavage by single chain catalytic components the hydrolytic activity of catalytic antibodies and single chain catalytic components is compared. The substrates are $^{125}I$-labeled peptides that contain the scissile bond identified in Example IX above, but have little sequence identity with VIP. This minimizes the role of residues distant from the scissile bond in substrate interactions with catalytic antibodies. For $Gln^{16}$–$Met^{17}$ cleaving catalytic antibodies, a suitable substrate is pancreatic polypeptide (PP). PP has only three sequence identities with VIP, two of which are at the potential scissile bond ($Gln^{16}$–$Met^{17}$). Substrates for other types of antibodies are chosen from the commercially available $^{125}I$-labeled peptides: e.g., ANP, insulin, somatostatin and endothelin. These peptides (about 100,000 cpm) are tested as substrates for intact or single chain antibodies using the experimental conditions employed to test cleavage rates for VIP as described in Example II. The reaction mixtures are extracted on C-18 cartridges and subjected to reverse phase HPLC. Appearance of radioactive peaks with retention times different from those of the intact peptides is suggestive of peptide hydrolysis by the antibodies. Substrates hydrolyzed in the preliminary screening are studied further for identification of scissile bonds. The methods are similar to those employed for identifying the scissile bonds in VIP, i.e. use of low specific activity $^{125}I$-labeled substrate, purification of peptide fragments by resolutive reverse phase HPLC, and identification of the fragments by amino acid sequencing.

D. Determination of The Ability of Intact and Single Chain Antibodies to Cleave Analogs of VIP VIP analogs containing amino acid substitutions at the scissile bond are synthesized for use as substrates. The substitutions are with residues that are dissimilar to the original residues or are similar in charge or shape. For example, ($Asn^{16}$, $Nle^{17}$) VIP and ($Ala^{16}$, $Ala^{17}$) VIP are tested as substrates for Gln[16]-Met[17] cleaving catalytic antibodies. The ability of intact and single chain antibodies to cleave these substrates is tested by resolutive reverse phase HPLC. These substrates are labeled with $^{125}$I at Tyr[10], as described for VIP(1–28) in Example II. Synthetic VIP (1–16), (Asn[16])VIP(1–16), (Ala[16])VIP(1–16) labeled at Tyr[10] with $^{125}$I prepared by methods similar to that used in Example II, which are well known to the art, are used as standards. Coelution of synthetic standards with radioactive peptides produced after treatment of substrates with antibodies is construed as evidence for cleavage between residues 16 and 17. The relative ability of these peptides to act as substrates for the catalytic antibodies and their single chains is determined by measuring $K_m$ and $k_{cat}$ using trichloroacetic acid to distinguish between intact and fragmented VIP.

EXAMPLE XI

Cloning and Expressing cDNA For Catalytic Components

A. Outline of the Cloning Strategy

Cloning of the catalytic component cDNA may proceed by one of three approaches. In the preferred approach, mRNA from clonal human hybridoma cell lines which produce catalytic VIP antibodies is employed as starting material. The cells are harvested and mRNA is extracted by standard methods known to the art. The cDNA is prepared by reverse transcription of the mRNA by standard methods known to the art. The cDNA for Fd- and L-chains is amplified by polymerase chain reaction (PCR) using appropriate primers as described below. The amplified cDNA is then ligated into expression vectors by standard methods, expressed separately in *E. coli*, and the properties of the expressed single chain antibodies determined.

The second approach avoids reliance on the availability of clonal antibody producing cells. The starting material is mRNA from Epstein Bar virus (EBV)-transformed peripheral blood lymphocytes. The cDNA is prepared and amplified by PCR as previously described, and an expression library is constructed. The cDNA library is expressed by standard methods in a mammalian cell line which is selected for the desirable property of a culture supernatant which shows a low background of VIP hydrolysis, and the resulting recombinant cells are then directly screened for hydrolytic VIP antibodies. The cDNA showing the highest VIP catalytic activity in mammalian cells is then further cloned in *E. coli* using known techniques optimized for overproduction of the expressed recombinant proteins.

A third method is screening for expression of recombinant Fab, using a randomly constructed, Fd- and L-chain combinatorial library using the method of Huse et al. (19).

B- preparation of Antibody Secreting Cells

Stable antibody-producing hybridomas of EBV-transformed lymphocytes and mouse/human heteromyeloma are constructed by standard methods of (20, 21). The hybrids are grown in the antibiotic G-418 to stabilize the human chromosomes. Treatment with Ouabain eliminates the parent EBV-lymphoblastoid cells. These heterohybrids are then screened for antibodies with VIP hydrolytic activity.

Screening of the antibodies is performed by incubation of culture supernates with (Tyr[10−125])VIP for 3 hours, undegraded VIP is precipitated with 10% TCA, the precipitate is trapped on GF/F filters using a Cambridge harvester, and the filters are counted for radioactivity. If the culture fluids are centrifuged (5000×g; to remove cellular debris) and diluted two-fold prior to assay, their background VIP-hydrolytic activity is negligible. This method permits screening of large numbers of wells in a single assay, and has been developed specifically to facilitate cloning of hydrolytic antibody producing cells. The TCA-precipitation method is unlikely to detect peptide bond cleavage close to the N- or C-terminii of VIP, since TCA would probably precipitate large $^{125}$I-labeled peptide fragments produced by such cleavages.

The screened hybrids are then cloned by limiting dilution using 0.3 cells/well with 10% Origen cloning factor (IGEN) in place of feeder layers to isolate clones producing monoclonal human anti-VIP catalytic antibodies.

C. Derivation of primers for PCR.

Catalytic antibody is purified from the culture supernatant of monoclonal hybridoma cells by chromatography on protein G-Sepharose. Sufficient quantities (about 50 µg) of the catalytic IgG molecule are dissociated into component H- and L-chains by reduction, alkylation and high performance gel filtration under denaturing conditions in a 6M urea containing buffer. A minimum of 15 N-terminal residues of both the H- and L-chains are determined using an Applied Biosystems liquid phase sequenator. This amino acid sequence information is used to derive synthetic oligonucleotides by standard methods, incorporating necessary alternative sequences to take into account codon degeneracy, with inosine placed in codons with the highest degeneracy level. These oligonucleotides serve as 5' variable region primers for cloning the Fd- and L-chain cDNA.

An alternative to sequencing of the antibody N-terminus is to use a mixture of consensus sequence primers for the antibody variable regions (22, 23). Primers for the constant regions are based on known sequences of the CH1 and CL domains, from Kabat and Wu's data base (24). In order to narrow down the sequence choices, the isotype of the antibody is determined using monospecific antisera directed against human IgG subclasses (Boehringer) in an ELISA assay, and the 3' oligonucleotide for CH1 is synthesized based on the type of H-chain. Likewise, the type of L-chain (kappa or lamba) is determined and the primer for CL is designed accordingly. The 5' $V_H$ and L-primers are constructed with a NotI restriction Site and the 3' CH1 and CL primers are constructed with a translation termination codon and a convenient NotI restriction site for subsequent forced cloning. Since NotI site is 8 bp in length, the likelihood of its presence in the cDNA clones of interest is low.

D. cDNA preparation, Amplification and Sequencing

Poly(A+)RNA is prepared from the catalytic antibody producing hybridoma cell line by the guanidinium thiocyanate/CsCl method followed by oligo(dT)-cellulose chromatography (25). All necessary precautions are taken to minimize RNase contamination in glassware and plastic wares. The cDNA is copied from the mRNA (5–10 µg) using reverse transcriptase an oligo(dT) primer and dNTP substrates as described in Example XI. The Fd- and L-chain cDNAs is then amplified using the polymerase chain reaction technique (PCR). For PCR amplification, the cDNA-RNA hybrids is then mixed with dNTPs and the 5' and 3' primers for Fd- and L-chains, Taq polymerase is added, and the sample overlaid with paraffin oil, 25 or more cycles performed, each cycle consisting of denaturation (92° C., 1 minute), annealing (52° C., 2 minutes) and elongation (72° C., 1.5 minutes). The amplified cDNA is then extracted with phenol, then with phenol/chloroform, ethanol precipitated and frozen.

For sequencing of Fd- and L-chain cDNA, the PCR products are purified on a 2% agarose gel, digested with NotI and ligated into a suitable vector of the pGEM series.

Dideoxynucleotide chain termination sequencing is carried using T7. DNA polymerase (26).

E. Cloning and Expression of Amplified DNA:

Standard DNA technology is employed to construct an expression vector suitable for cloning of the amplified cDNA for Fd- and L-chains. The sequence of the oligonucleotides used to construct the vector includes elements for construction, expression and secretion of the recombinant proteins. The vector is tailored for high level expression by known methods. The vector is the pER vector which contains appropriate restriction sites, the vX polylinker region, an ampicillin resistance gene and a strong run promoter (E. coli ribosomal RNA promoter) under the control of the lac operator. The ribosomal RNA promoter in pER vector is highly induced during cell growth while the lac operator confers lactose or isopropylthiogalactoside (IPTG) inducibility to the expression (27). The amplified cDNAs derived contain only the mature Fd- or L-chain coding sequences. To facilitate secretion of $V_H$ and $V_L$ into the E. coli periplasm, the leader peptide sequence for the bacterial pel B gene is incorporated into the vector (28, 29). cDNA amplified by PCR is digested with Notl, fragments are phenol-extracted, purified on 2% agarose gels and the insert ligated to the expression vector digested with Notl. E. coli is transformed with recombinant plasmids using calcium chloride, colonies grown with ampicillin to select successful recombinants incorporating a gene for ampicillin resistance, resistant colonies toothpicked into medium containing ampicillin, and the cells grown in IPTG to induce expression. After about 24 hours, the supernatant is separated from the cells, the cells are shocked hypo-osmotically to release periplasmic contents and the supernatant of the lysate is collected. Since the Fd- and the L-chain are secreted into the E. coli periplasm, the moderate level of expression from the lac promoter should not result in toxicity due to the "jamming of membrane protein traffic." (30).

Fd- and L-chains are initially fractionated from the lysate and the culture supernate by high performance gel filtration, and fractions with molecular mass 20–30 kD are purified further by immunoaffinity chromatography as described in Example IX. Since the recombinant Fd- and L-chains contain the CH1 and CL domains, immobilized monoclonal anti-human Fd (sUpplied by Dr. S. Rodkey) and rabbit anti-human L-chain antibodies (Accurate) are used for the immunoaffinity chromatography. The antibodies are purified by chromatography on protein G-Sepharose and covalently coupled to CNBr-Sepharose using standard methods.

SDS-PAGE silver staining and immunostaining with specific anti-H-chain and anti-L-chain antibodies using a PHAST system are performed to confirm the identity and purity of the recombinant proteins as described in Example IX. Assay of (Tyr$^{10-125}$) VIP hydrolytic activity is performed to monitor recovery of Fd- and L-chains during purification.

The purified Fd- and L-chains are subjected to N-terminal amino acid sequencing. Identity of the N-terminal residues of the recombinant proteins and the original antibody H- and L-chains confirms that the correct molecules have been cloned.

EXAMPLE XII

Cloning from EBV Transformed Lymphocytes

In an alternative cloning method, cDNA for Fd- and L-chains is prepared from EBV-transformed patient lymphocytes, ligated into an appropriate vector, expressed in eukaryotic cells and screened for VIP hydrolytic activities (31–34). Although it is a tedious matter to isolate the cDNA for catalytic antibodies from a mammalian expression library, this method has advantages because the cDNA for Fd- and L-chains are short (approximately 650 bases) and can be selectively amplified from poly(A+)RNA by polymerase chain reaction. Moreover, it is necessary to resort to screening for expression in a mammalian cell line, since high rates of background hydrolysis of VIP in culture supernates and lysates of E. coli transformed with expression vectors has been observed (during development of these methods). In contrast, culture supernates from irrelevant myeloma cells, hybridoma cells and EBV-transformed cells show little background VIP-hydrolytic activity (FIG. 8).

A. Primers for PCR

Since mRNA species coding for many antibody molecules are likely to be present in the starting EBV-transformed cells, the "anchored PCR" method described by Loh and coworkers (35) is used to amplify all possible Fd- and L-chain cDNAs. The method is based on the attachment of a poly(dG) tail to the first cDNA strand, and the use of a complementary poly(dC) primer for second strand synthesis by PCR (see below). The poly(dC) primer for this example contains a Notl Notl restriction site for forced cloning. This primer substitutes for the V-region primers described in Example XI above, and amplifies the 5' ends of Fd- and L-chain cDNA. Primers for the constant regions are based on known sequences of the CH1 and CL domains, from Kabat and Wu's data base (24). As described in Example XI the sequence choices are narrowed by determining the isotype of the antibody. This is done by precipitating the hydrolytic activity present in the culture supernates of EBV-transformed lymphocytes with monospecific antisera directed against human IgG subclasses (Boehringer). The oligonucleotide primers for CH1 are then synthesized based on the type of H-chain, incorporating necessary degeneracies. Likewise, the type of L-chain (kappa or lamba) is determined and the primer for CL is designed accordingly. The 3' CH1 and CL primers contain a translation termination codon and a convenient Notl restriction site for subsequent forced cloning. Since the Notl site is 8 bp in length, the likelihood of its presence in the cDNA clone of interest is low.

D. cDNA preparation and Amplification

Poly(A+)RNA is prepared from the catalytic antibody producing EBV-transformed patient lymphocytes by the method described for hybridoma cells. The first cDNA strand is synthesized using appropriate constant region primers for Fd- and L-chains. A poly(dG) tail is then added to the first strand DNA by treatment with terminal deoxynucleotide transferase in dGTP for 1 hour. The reaction is stopped by heating to 70° C., and the DNA is recovered by ethanol precipitation. The poly(dG) tail on the first strand serves as the complementary sequence for the poly(dC) 5' primer during second strand synthesis, catalyzed by the Taq polymerase. Twenty five or more PCR cycles are performed to achieve amplification.

C. Cloning and Expression of Amplified DNA

The cDNA is then cloned via the Notl site into the mammalian expression vector H3M by known methods (36). The π H3M vector contains the SV40 origin of replication which allows template amplification in COS cells, a chimeric CMV/HIV enhancer promoter that drives the expression of the cloned sequences and SV40 small t splice and polyadenylation signal. Since the π H3M vector is πVX/supF-based the resultant recombinant DNAs are transformed into MC1061/P3 strain which is suitable for their maintenance. Bacteria are then transformed with the cDNA library. The bacterial transformants containing the library are maintained on filters. Transformants are divided into pools and miniprep DNA prepared for transfection into COS cells by the calcium phosphate method (37). The culture supernatants from tranfected cells are then assayed for the catalytic component using (Tyr$^{10-125}$)VIP as substrate. The DNA pool showing the highest activity is then further screened until the clone for the optimal catalytic antibody is obtained. Once the cDNA has been cloned, methods similar to those described in Example 12 are used to: (i) express Fd- and L-chains in bacteria, (ii) purify Fd- and L-chains, (iii) reconstitute Fab from the single chains, and (iv) determine the catalytic activity of single Fd- and L-chains, and reconstituted Fab.

EXAMPLE XIII

FORMATION OF FAB BY RECOMBINANT Fd- AND L-CHAINS

Recombinant Fd- and L-chains are mixed for 12 hours at pH 8.5, permitting spontaneous reconstitution of Fab (12, 14). An increase in molecular mass, judged by gel filtration and/or native gel electrophoresis and immunoblotting with anti-H-chain and anti-L-chain antiserum are evidence for formation of Fab. The catalytic properties ($k_{cat}K_m$ and specificity) of recombinant Fd, L-chains and Fv are determined as in Example X.

EXAMPLE XIV

Preparation of Fv Fragment

A. preparation of Fab'

The Fab' fragment is prepared by the method of Inbar et al. (38).

One gram of catalytic antibody as derived from Example V, in eluting buffer (0.15M NaCl 0.01M sodium phosphate buffer at pH 7.4), is adjusted to pH 4.7 by the addition of 0.5M sodium acetate buffer, pH 4.5 (one tenth of total volume), and then 10 mg pepsin (in 1 ml of 0.005M sodium acetate, Ph 4.5) is added. The mixture is incubated for six hours at 37° C. and then centrifuged to remove precipitate. The supernatant is adjusted to pH 8 and applied to a column (3×14 cm) of VIP-Sepharose. The Fab' fragment is eluted from the column with 0.05M VIP-glycine in eluting buffer. Activity of the purified Fab' is assayed by a kinetic analysis of the cleavage of labelled VIP as in example II.

B. preparation of Fv Fragment

The Fv fragment is prepared from the catalytic antibody of Example V or from an Fab' fragment of subsection A above. Either the antibody or the Fab' fragment is cleaved to the Fv fragment by the method of Hochman et al. (15).

The Fab' fragment or antibody (10 mg/ml in 0.15M NaCl, 0.01M sodium phosphate buffer at pH 7.4) is adjusted to ph 3.8 by the addition of 1M sodium acetate, pH 3.7 (one tenth of total volume). To the turbid protein solution, pepsin (10 mg/ml in 0.01M sodium acetate, pH 3.7) is added to give a weight ratio of 1:100 of enzyme to Fab'. After four hours at 37° C. the digestion is terminated by adjusting the pH to 7.0 with 2M Tris-HCl, pH 8.2. Precipitate not dissolved by the rise in pH is removed by centrifugation. The supernatant is applied to a Dnp-lysine Sepharose column equilibrated and run with 0.05M NaCl-003M, pH 7.4). After washing the unabsorbed fraction, the column is eluted with VIP-glycine (0.05M, pH7.4) and the yellow fraction collected, concentrated by vacuum dialysis, and applied to a Sephadex G-75 column, to separate Fv from undigested Fab' by the method of Hochman et al. (39). For the affinity chromatography step 1 ml of VIP-lysine is used per 2 mg of digest and 0.3 ml of VIP-glycine is used for elution.

Catalytic activity of the purified Fv is assayed by a kinetic analysis of the cleavage of $^{125}$I-labeled VIP as in example II. The molecular weight of the Fv is about 25 kD as measured by sedimentation equilibrium (39).

EXAMPLE XVI

Separation of Fv into $V_L$ and $V_H$ Fragments

The heterodimer Fv is separated into its H- and L-chain derived components by the method of Hochman et al. (39). Briefly, Fv is chromatographed in 8M urea at pH 9.0 on DEAE-cellulose.

Alternatively, the separation is performed by the method of Example VIII wherein Fv is substituted for the Fab.

The H- and L-chain fractions produced by either method are distinguished by staining with anti H-chain and anti L-chain antibodies by the standardized immunoblotting method of Example IX. Catalytic activity of the purified Fv is assayed by a kinetic analysis of the cleavage of $^{125}$I-labeled VIP as in example II. The molecular weight of the separate $V_L$ and $V_H$ chains is about 12.5 kD as determined by sedimentation equilibrium (39).

EXAMPLE XVII

Preparation of Catalytic Antibody Component Interleukin 2 Fusion Protein

A fusion protein consisting of an interleukin 2 and an Fv catalytic antibody component able to catalytically activate a prodrug to a drug, or a protoxin to a toxin able to regulate activated T-cells is prepared by the following method.

To prepare a catalytic antibody fusion protein a plasmid is assembled essentially as described by Chaudhaury et el. (40), employing a DNA segment derived from a catalytic monoclonal antibody, encoding the $V_H$ joined to a DNA segment encoding the $V_L$ by a 45-bp linker. The $V_L$ sequence is in turn joined to a DNA segment encoding interleukin-2 (FIG. 9). The assembled genes is under the control of the T7 promoter.

The source catalytic antibody is prepared by the methods taught by U.S. Pat. No. 4,888,281. A compound representing an analog to the intermediate transition state of the reaction of protoxin to toxin is synthesized. That compound is then prepared with appropriate adjuvents and used to induce B cells to produce antibodies. The B cells are screened to identify clones which produce an antibody able to catalyze the protoxin to toxin reaction.

The DNA sequences for catalytic $V_H$ and $V_L$ components are derived by one of several methods. One method is to prepare the cDNA by reverse engineering (preparing an oligonucleotide encoding for a known peptide sequence) by methods well known to the art, from the peptide sequences of $V_H$ and $V_L$ components prepared by the methods of Examples XIII through XVI. Another method is to prepare the cDNA by reverse transcription of mRNA isolated from cells producing the desired protein, followed by amplification by PCR as described above in Examples XI and XII. The cDNA sequence for interleukin 2 is obtained from Biotech Research Laboratories of Rockville Maryland as a plasmid. The sequence encoding the $V_H$—{45 bp linker}—VL linked to an ampicillin resistance gene is inserted into the plasmid carrying the IL-2 gene downstream of the IPTG inducable T7 promoter by methods well known to the art.

The fusion protein is injected into an animal where the IL-2 moiety causes it to selectively bind to or associate with activated T-cells. The protoxin or prodrug is then administered. The protoxin or prodrug which reaches the bound or associated fusion protein is cleaved by the catalytic moiety to the active drug or toxin which kills the T cell without producing significant toxicity to other tissues. This method of treatment is useful for the treatment of a wide variety of disorders, e.g., adult T-cell leukemia or autoimmune diseases or autoimmune reactions for which the removal of T cells is desirable for curative or palliative purposes.

Example XVIII

Activation of a Prodrug Using a Catalytic Antibody Component as a Glycoside Antimetabolites are compounds that interfere in either the biosynthesis, utilization, or metabolic function of normal cellular metabolites. To be successfully selective in the chemotherapy of tumors, an antimetabolite should adversely affect one or more vital metabolic reactions in the tumor without seriously endangering normal tissues.

Some of the most successful anticancer drugs have been those based on purine or pyrimidine analogs whose activity is dependent on their ability to inhibit DNA or RNA synthesis. One such drug is arabinosyl cytosine (I) (cytaribine, Ara C or CA) whose activity as an inhibitor of DNA synthesis derives from the presence of arabinose in place of ribose, the difference being in the stereochemistry of the 2' hydroxy group. Ara C is administered in the free 5'-hydroxyl form and only becomes activated after entry into cells by phosphorylation to the 5'-triphosphate form. Thus, it is already a prodrug, but when administered systemically, its activation can take place in any cell, tumor or normal, into which the drug enters. As a result of the wide systemic distribution of the drug, numerous side effects occur, such as nausea, vomiting, alopecia, myelosuppression, etc.

It has now been found that Ara C can be modified to a prodrug form in which spontaneous intracellular activation would be reduced. First, a biological binding agent is selected based upon the tissue being targeted. This can be interleukin-2 as described in Example XVII if the target tissue consists of lymphoid cells, e.g. T4 cells, or the binding agent can be an antibody or component of an antibody selected for its ability to bind to a target tumor tissue, the binding agent being either chemically or genetically linked to a catalytic component, as described in previous examples, and able to catalytically convert the prodrug to drug. Second, the pro form of Ara C is administered and its activation is then restricted to those tissues bearing the catalytic component activity. Thus a more favorable discrimination of tumor and normal tissue results. Since Ara C has a very short plasma half-life, diffusion of the activated drug away from the tumor site is followed by rapid deactivation before significant systemic toxicity results.

Synthesis of 5'-galactosyl Ara C and its transition state analog

The synthesis of the amidine galactosyl analog of Ara C [15] is outlined in Schemes 2 and 3 (FIGS. 11, 12) The tribenzoylated derivative [3] from Scheme 1 (FIG. 10) is converted to [9] by treatment with methanesulfonyl chloride in pyridine followed by displacement with lithium azide in the N,NM-dimethylformamide at 75° C. Hydrogenation of [9] in ethanol at 50 psi of hydrogen pressure in the presence of 10% palladium on charcoal affords the 4' amino derivative.

The β-galactonolactam [13] is prepared by first treating 2,3,4,6-tetra-D-benzyl-2-d-galacto-pyranose [(11)] with dimethyl sulfoxide and acetic anhydride to give 2,3,4,6,-tetra-O-benzyl-D-Galactono-1,5-lactone [12] which is then condensed with aqueous ammonia (25% w/w) solution in the presence of trace amounts of Amberlite 1R 120 $H^+$ in dioxane for 6 hrs to afford [13]. Conversion of [13] to its imido ester analog by treating it with trimethyloxonium tetrafluorobarate followed by its reaction the 5' amino derivative [10] yields the fully protected amidine galactosyl analog [14]. Deprotection using hydrogenation at 50 psi of hydrogen pressure in the presence of 10% palladium on charcoal followed by treatment with concentrated aqueous ammonia gives [15].

The synthesis of the 5'-beta-D-galactose analog of cytosine-beta-D-Arabinofuranoside [5] is outlined in Scheme 1 (FIG. 10).

Treatment of Ara C [1] with Bis (P-methoxyphenyl) phenyl methyl chloride in pyridine, followed by tribenzoylation using benzoyl chloride and then detritylation of [2] with trichloroacetic acid in dichloromethane, affords the partially protected derivative [3]. Dilute aqueous acid treatment of beta-D-galactose pentaacetate [6] followed by treatment with sodium hydride and excess trichloroacetonitrile yields the trichloroacetimidate [8]. Coupling of [8] with [3] in the presence of the Lewis acid boron trifluoride etherate in dichloromethase gives [(4)]. The 5'-beta-D-galactose analog of Ara C [5] is obtained after the complete deprotection of [4] using concentrated aqueous ammonia.

Production of antibodies and screening for Binding to Transition state Analogs

Monoclonal antibodies to [15] in Scheme 3 (FIG. 12), after conjugation to a suitable carrier, are produced essentially as described in Example 1. Antibody-producing clones are first screened for their ability to bind to the Ara C analog [15] by methods similar to those described U.S. Pat. No. 4,888,281.

In vitro catalytic activity assay

Those antibody clones displaying binding activity for [15] are screened for their ability to cleave the galactosyl moiety from the Ara C substrate [5] by an assay essentially as described in Koerner and Nieman (41), but substituting galactose oxidase for glucose oxidase. The principle of the assay is the detection of galactose as it is released from the prodrug by the catalytic antibody using a galactose oxidase/luminol chemiluminescence procedure.

The catalytic antibodies showing the desirable property are then used to produce one or more useful components as described in Examples V, VII, VIII– XIV above. The use of catalytic components instead of an intact catalytic antibody provides the advantage of a smaller molecular weight, thus permitting better tissue penetration.

In vivo assays

The conversion of galactosyl Ara C to Ara C by the catalytic antibody component in the presence of target cells results in inhibition of DNA synthesis and cell-killing. A simple assay of DNA synthesis is carried out essentially as described in Gish et al. (42), in which the ability of Ara C to inhibit DNA synthesis in phytohaemagglutin (PHA) stimulated human lymphocytes, using a tritiated thymidine incorporation assay, is measured.

REFERENCES

1. Janda et al. *Science* 241: 1188–1191 (1988).
2. Baldwin, E. and Schultz, P. G. *Science* 245: 1104–1107 (1989).
3. Iverson and Lerner, *Science* 243: 1184 (1989).
4. *Proceedings of the Synposium of Immunological Recognition* Vol VII, published by Springer Verlag (1989).
5. Paul, S., Volly, D. J., Beach, C. M., Johnson, D. R., Powell, M. J., Massey, R. J. *Science* 244: 1158–62 (1989).

6. Roholt, O., Onoue, K., and Pressman, D. *Biochemistry* 51: 173 (1964).
7. Ward, E. S., Gussow, D. Griffiths, A. D., Jones, P. T. and Winter, G. *Nature,* 341: 544–546 (1989).
8. Edelman, G. M., Olins, D. E., Gally, J. A. and Zinder, N. D. *Proc. Natl. Acad. Sci.,* 50: 753–761 (1963).
9. Franek, F. and Nezlin, R. S. *Folia Microbiol.,* 8: 128–130 (1963).
10. Franek, F. and Nezlin, R. S. *Biokhimiya,* 28: 193 (1963).
11. Porter, R. R. and Weir, R. C. *J. Cell Physlol.* 67 (Suppl. 1): 51–64 (1966).
12. Jaton, J.-C., Klinman, N. R., Givol, D. and Sela, M. *Biochemistry,* 7: 4185–4195 (1968).
13. Roholt, O. Onoue, K. and Pressman, D. *Proc. Natl. Acad. Sci.,* 51: 173–178 (1963).
14. Powell, M. J., Massey, R. J., and Rees, A. R. PCT/US89/01950, international publication No. WO89/10754, International publication date 16 Nov. 1989.
15. Hochman, J. Inbar, D. and Givol, D, *Biochemistry* 12: 1130 (1973).
16. *Affinity Chromatography Principles and Methods,* pharmacia, Uppsula Sweden pp. 12–18 (1986).
17. Paul, S., Volle, D. J., Beach, C. M., Johnson, D. R. Powell, M. J. and Massey, J. J. *Science,* 244: 1158–1162 (1989).
18. Pharmacia, Handbook, *FPLC Ion Exchange and Chromatofocusing—Principles and Methods,* pp. 59 to 106.
19. Huse, W. D., Sastry, L., Iverson, S. A., King, A. S., Alting-Mees, M., Burton, D. R., Benkovic, S. J. and Lerner, R. A. *Science,* 246: 1275–1281 (1989).
20. Roder, J. C., Cole, S. P. C. and Kozbor, D. *Methods in Enzymology,* 121: 140–167 (1986).
21. Kozbor, D. and Rodor, J. C. *Immunology Today,* 4: 72–79 (1983).
22. Orlandi, R., Gussow, D. H., Jones, P. T. and Winter, G. *Proc. Natl. Acad. Sci. USA,* 86: 3833–3837 (1989).
23. Sastry, L., Alting-Mees, M., Huse, W. D., Short, J. M., Sorge, J. A., Hay, B. N., Janda, K. D. Berkovic, S. J. and Lerner, R. A. *Proc. Natl. Acad. Sci. USA,* 86: 5728–5732, (1989).
24. Kabat, E. A., Wu, T. T., Reid-Miller, M., Perry, H. M. and Gottesman, K. S.: Sequences of proteins of immunological interest (4th ed.), U.S. Department of Health and Human Services.
25. MacDonald, R. J., Swift, G. H. Przbyla, A. E. and Chirgwin, J. M. *Meth, Enzymol,* 152: 219–226 (1987).
26. Mierendorf, R. C. and Pfeffer, D. Meth. Enzymol, 152: 556–562 (1987).
27. Giam, C.-Z. and Boros, I. *J. Biol. Chem.,* 263: 14617–14620 (1988).
28. Skerra, A. and Pluckhun, A. *Science,* 240: 1038–1043 (1988).
29. Better, M., Chang, C. P., Robinson, R. R. and Horwitz, A. H. *Science,* 240: 1041–1043 (1988).
30. Emr, S. D., Hedgpath, J., Clement, J. M., Silhavy, J. J., and Hofnung, M. *Nature,* 285: 82–85 (1980).
31. Wong, G. G., Witek, J. S., Temple, P. A., Wilkens, K. M., Leary, A. C., Luxenberg, D. P., Jones, S. S., Brown, E. L., Kay, R. M., Orr, E. C., Shoemaker, C., Golde, D. W., Kaufman, R. J., Hewick, R. M., Wang, E. A. and Clark, S. C. *Science,* 228: 810–815, (1985).
32. Lee, F., Yokota, T., Otsuku, T., Meyerson, P., Villaret, D., Coffman, R., Mosmann, T., Rennick, D., Roehm, N., Smith, C., Zlotnik, A. and Arai, K.-I. *Proc. Natl. Acad. Sci., USA* 83: 2061–2065 (1986).
33. Yokota, T., Otsuka, T., Mosmann, T., Banchereau, J., DeFrance, T., Blanchard, D., De Vries, J. E., Lee, F. and Aral, K.-I. *Pro. Natl. Acad. Sci., USA,* 83: 5894–5896 (1986).
34. Yang, Y.-C., Clarietta, A. B., Temple, P. A., Chung, M. P., Kovacic, S., Witek-Giannotti, J. S. Leary, A. C., Kriz, R., Donahue, R. E., Wong, G. G. and Clark S. C. *Cell,* 47: 3–10 (1986).
35. Loh, E. Y., Elliot, J. F., Cwiria, S., Lanier, L. L. and Davis, M. M. *Science,* 243: 217–220 (1989).
36. Aruffo, A. and Seed, B. *Proc. Natl. Acad. Sci.,* 84: 8573–8577 (1987).
37. Van der Eb, A. J. and Graham, F. L. *Meth. Enzymol.,* 65: 826–839 (1980).
38. Inbar, D, Rotman, M and Givol, D *J. of Biol. Chem.* 246: 6272 (1971).
38. Inbar, D, Rotman, M and Givol, D. *J. of Biol. Chem.* 246: 6272 (1971).
39. Hochman, J. Inbar, D, and Givol, D., *P.N.A.S.* (U.S.A.) 69: 2659 (1972).
40. V. J. Chaudhary et al., *Nature* 339: 394 (1989).
41. Koerner and Nieman *J. Chromatography* 449, 216–228 (1988).
42. Gish et al, *J. Med. Chem.* 14: 1159–1162, 1971)

What is claimed is:

1. A catalytic component part of an antibody which is capable of catalyzing cleavage of a peptide bond, said catalytic component part being selected from the group consisting of a light chain, a heavy chain, an Fd fragment, an unassociated mixture of a light and heavy chain, a variable fragment of a light chain, a variable fragment of a heavy chain, a catalytic domain of a light chain, a catalytic domain of a heavy chain, a heterodimer consisting of a heavy chain and a light chain, a heterodimer consisting of an Fd fragment and a light chain associated non-covalently, a heavy chain homodimer and a light chain homodimer.

2. A catalytic component part of an antibody which is capable of catalyzing cleavage of a peptide bond, said catalytic component part being selected from the group consisting of an Fab Fragment and an Fv Fragment.

3. A catalytic component part of an antibody having catalytic properties as recited in claim 1 wherein said catalytic component part is a heavy chain.

4. A catalytic component part of an antibody having catalytic properties as recited in claim 1 wherein said catalytic component part is an unassociated mixture of a light and heavy chain.

5. A catalytic component part of an antibody having catalytic properties as recited in claim 1 wherein said catalytic component part is a variable fragment of a light chain.

6. A catalytic component part of an antibody having catalytic properties as recited in claim 1 wherein said catalytic component part is a variable fragment of a heavy chain.

7. A catalytic component part of an antibody having catalytic properties as recited in claim 1 wherein said catalytic component part is a catalytic domain of a light chain.

8. A catalytic component part of an antibody having catalytic properties as recited in claim 1 wherein said catalytic component part is a catalytic domain of a heavy chain.

9. A catalytic component part of an antibody having catalytic properties as recited in claim 1 wherein said catalytic component part is a heavy chain homodimer.

10. A catalytic component part of an antibody having catalytic properties as recited in claim 2 wherein said catalytic component part is the Fv portion of an antibody.

11. A catalytic component part of an antibody having catalytic properties as recited in claim 2 wherein said catalytic component part is a heterodimer.

12. A catalytic component part as recited in claim 1 wherein said catalytic component part is a chimeric product expressed by a nucleic acid sequence coding for a continuous polypeptide sequence which contains an antibody component part having catalytic activity, and at least one other protein, said nucleic acid sequence comprising:

(a) a first nucleic acid sequence coding for said catalytic component part; and (b) at least one additional nucleic acid sequence coding for at least one additional protein, wherein said antibody component part having catalytic activity is able to catalytically cleave a prodrug or protoxin into a drug or toxin and said additional protein is able to bind the target cell of said prodrug or protoxin.

13. A method for preparing a catalytic domain comprising the steps of:

(a) determining the sequence of the variable region of a catalytic antibody;

(b) inserting into a cell a gene coding for the variable region of said catalytic antibody; and (c) expressing said variable region in said cell, wherein said inserted gene codes for a fragment of said variable region.

14. A method for preparing a catalytic domain comprising the steps of:

(a) determining the sequence of the variable region of a catalytic antibody;

(b) inserting into a cell a gene coding for the variable region of said catalytic antibody; and (c) expressing said variable region in said cell, wherein said cell is selected from the group consisting of a bacteria, a fungus, a yeast, an animal cell, a protozoan cell, and a plant cell.

15. A method for preparing a catalytic domain comprising the steps of:

(a) determining the sequence of the variable region of a catalytic antibody;

(b) inserting into a cell a genes coding for the variable region of said catalytic antibody; and (c) expressing said variable region in said cell, wherein said gene is subjected to mutagenesis before insertion into said cell.

16. A method for preparing a catalytic domain comprising the steps of:

(a) determining the sequence of the variable region of a catalytic antibody;

(b) inserting into a cell a gene coding for the variable region of said catalytic antibody; and (c) expressing said variable region in said cell, wherein said genes is subjected to mutagenesis after insertion into said cell.

17. A method for selecting a gene fragment coding for a catalytic component part of an antibody which comprises the steps of:

(a) selecting at least one genes fragment coding for a catalytic component part;

(b) inserting said genes fragment into a cell under conditions suitable for the expression of said variable region; and (c) screening said cells for those which express a catalytic component part, wherein said genes fragment codes for a catalytic component part selected from the group consisting of a light chain, a heavy chain, a variable fragment of a light chain, a variable fragment of a heavy chain, a catalytic domain of a light chain, a catalytic domain of a heavy chain, and an Fd fragment.

18. A method for the preparation of a bifunctional chimeric product comprising a catalytic component part of an antibody and a second protein by expressing a nucleic acid sequence coding for a continuous polypeptide sequence which contains an antibody component part having catalytic activity, and at least one other protein, said nucleic acid sequence comprising:

(a) a first nucleic acid sequence coding for said catalytic component part; and (b) at least one additional nucleic acid sequence coding for at least one additional protein, wherein said antibody component part having catalytic activity is able to catalytically cleave a prodrug or protoxin into a drug or toxin and said additional protein is able to bind the target cell of said prodrug or protoxin.

19. A method for preparing a catalytic component part of an antibody which comprises:

(a) subjecting said antibody to conditions suitable for the fragmentation of said antibody into components selected from the group consisting of a light chain, a heavy chain, an Fd fragment, an unassociated mixture of a light and heavy chain, a variable fragment of a light chain, a variable fragment of a heavy chain, a catalytic domain of a light chain, a catalytic domain of a heavy chain, a heterodimer consisting of one light and one heavy chain, a heterodimer consisting of a Fd fragment, a light chain linked by non-covalent bonding, a heavy chain homodimer, and a light chain homodimer;

(b) screening said components for catalytic activity; and (c) obtaining the desired catalytic component.

20. A method for preparing a heterodimer which is capable of catalyzing cleavage of a peptide bond, said heterodimer being a catalytic component part of an antibody, comprising the steps of:

(a) identifying an antibody of interest;

(b) cleaving said antibody into at least two heterodimers; and (c) screening said heterodimers for catalytic activity.

21. A method for preparing a heterodimer which is capable of catalyzing cleavage of a peptide bond, said heterodimer being a component part of an antibody, comprising the steps of:

(a) identifying an antibody-producing cell line; and (b) screening said cell line for a cell which expresses catalytic heterodimers, wherein said antibody is catalytic.

22. A method for preparing a homodimer which is capable of catalyzing a chemical reaction, said homodimer being assembled from light or heavy chains of an antibody, comprising the steps of:

(a) identifying an antibody of interest;

(b) separating the light and heavy chain components of said antibody;

(c) subjecting the light or heavy chains to conditions promoting the formation of light or heavy chain homodimers; and (d) screening said homodimers for catalytic activity, wherein said antibody is catalytic.

23. A method for preparing a component part of an antibody which component part is capable of catalyzing a chemical reaction, comprising the steps of:

(a) identifying an animal with an autoantibody to a self-antigen of the animal;

(b) isolating a serum fraction containing a plurality of autoantibodies;

(c) screening the serum fraction obtained in step (b) to identify an autoantibody which binds to a substrate of the said reaction; and (d) screening components of said autoantibody to obtain a catalytic component of said autoantibody, wherein said component part is a component part of a catalytic autoantibody.

24. A method for preparing a component part of an antibody as recited in claim 1, said component part being capable of catalyzing a chemical reaction wherein said chemical reaction is known to be catalyzed by an enzyme, comprising the steps of:

(a) generating a plurality of monoclonal antibodies to said enzyme;

(b) screening said plurality of monoclonal antibodies to identify a first monoclonal antibody which inhibits binding of the reactant to the enzyme;

(c) recovering the said first monoclonal antibody;

(d) generating a plurality of anti-idiotype monoclonal antibodies to the said first antibody recovered in step (c);

(e) screening said plurality of anti-idiotype monoclonal antibodies generated in step (d) to identify a second monoclonal antibody which binds the reactant and catalytically increases the rate of the reaction;

(f) producing a quantity of the monoclonal antibody identified in step (e) by culturing a plurality of hybridoma cells, each of which produces said monoclonal antibody; and (g) obtaining a catalytic component of said monoclonal antibody.

25. A method for preparing a catalytic light or catalytic heavy chain of an antibody comprising the steps of dissociating said antibody into light and heavy chains and identifying the catalytic light or catalytic heavy chains.

26. A method as recited in claim 25 comprising the steps of:

(a) cleaving said antibody into Fab and Fc fractions; and (b) reducing and then alkylating said Fab fraction to cleave bonds connecting light and heavy chains.

27. A catalytic component part of an antibody selected from the group consisting of a light chain, a heavy chain, a Fd fragment, an unassociated mixture of a light and heavy chain, a variable fragment of a light chain, a variable fragment of a heavy chain, a catalytic domain of a light chain, a catalytic domain of a heavy chain, a heterodimer consisting of one light and one heavy chain, a heterodimer consisting of a Fd fragment and a light chain linked by non-covalent bonding, a heavy chain heterodimer, and a light chain heterodimer, said component part having catalytic properties and having been prepared by:

(a) subjecting an antibody to conditions suitable for the fragmentation of said antibody into components;

(b) screening said components for catalytic activity; and (c) obtaining said catalytic component, wherein said antibody is catalytic.

28. A catalytic domain prepared by the process comprising the steps:

(a) determining the sequence of the variable region of a catalytic antibody;

(b) synthesizing an overlapping series of homologous peptide sequences representing sections of the sequence of said variable region;

(c) screening said series of homologs to select a homologous peptide sequence having desirable catalytic properties; and (d) synthesizing the selected peptide sequence.

29. A catalytic domain prepared by the process comprising the steps:

(a) determining the sequence of the variable region of a catalytic antibody;

(b) inserting into a cell a gene coding for the variable region of said catalytic antibody;

(c) expressing said variable region in said cell.

30. A catalytic component part of an antibody prepared by the process comprising the steps:

(a) inserting into a cell at least one nucleic acid sequence coding for a variable region of said antibody;

(b) subjecting said nucleic acid sequence to mutagenesis before insertion;

(c) screening the cell and its progeny for the presence of mutated variable regions of said antibody demonstrating desired catalytic activity;

(d) replicating said cell; and (e) expressing said mutated nucleic acid sequence to produce a translation product with the desired catalytic activity, wherein the antibody is catalytic.

31. A catalytic component part of an antibody prepared by a process comprising the steps of:

(a) identifying an animal with an autoantibody to a self-antigen of the animal:

(b) isolating a serum fraction containing a plurality of said autoantibodies;

(c) screening the serum fraction obtained in step (b) to identify an autoantibody which binds to a substrate of the said reaction; and (d) screening components of said autoantibody to obtain a catalytic component of said autoantibody.

32. A catalytic Fv component part of an antibody able to catalyze cleavage of a peptide bond, said Fv having been produced by a method comprising the steps of:

(a) selectively cleaving an antibody by contacting said antibody with pepsin to produce a mixture of fragments including the Fv component; and (b) treating the mixture such that the Fv component part is purified.

33. A method for catalyzing a chemical reaction comprising contacting a reactant with a catalytic component part of an antibody, said component being selected from the group consisting of a light chain, a heavy chain, an Fd fragment, an unassociated mixture of a light and heavy chain, a variable fragment of a light chain, a variable fragment of a heavy chain, a catalytic domain of a light chain, a catalytic domain of a heavy chain, a heterodimer consisting of one light and one heavy chain, a heterodimer consisting of a Fd fragment and a light chain associated non-covalently, a heavy chain homodimer, and a light chain homodimer.

34. A method for catalyzing cleavage of a peptide bond comprising contacting a reactant or reactants with a catalytic component part of an antibody selected from the group consisting of an Fab fragment and an Fv fragment.

* * * * *